(12) United States Patent
Tsuchida

(10) Patent No.: US 10,470,289 B2
(45) Date of Patent: Nov. 5, 2019

(54) TARGET FOR NEUTRON-GENERATING DEVICE AND MANUFACTURING METHOD THEREFOR

(71) Applicant: Yagami Co., Ltd., Nagoya-shi, Aichi (JP)

(72) Inventor: Kazuki Tsuchida, Tokyo (JP)

(73) Assignee: Yagami Co., Ltd., Nagoya-shi (JP)

( * ) Notice: Subject to any disclaimer, the term of this patent is extended or adjusted under 35 U.S.C. 154(b) by 223 days.

(21) Appl. No.: 14/414,252

(22) PCT Filed: Jul. 11, 2013

(86) PCT No.: PCT/JP2013/069046
§ 371 (c)(1),
(2) Date: Jan. 12, 2015

(87) PCT Pub. No.: WO2014/010704
PCT Pub. Date: Jan. 16, 2014

(65) Prior Publication Data
US 2015/0216029 A1  Jul. 30, 2015

(30) Foreign Application Priority Data

Jul. 13, 2012 (JP) ................................ 2012-158095
Oct. 9, 2012 (JP) ................................ 2012-224172

(51) Int. Cl.
*H05H 6/00* (2006.01)
*B22D 19/00* (2006.01)
(Continued)

(52) U.S. Cl.
CPC ............... *H05H 6/00* (2013.01); *B22D 19/00* (2013.01); *B23K 20/021* (2013.01); *A61N 2005/109* (2013.01); *G21G 4/02* (2013.01)

(58) Field of Classification Search
CPC . H05H 6/00; H05H 3/06; B22D 19/00; B23K 20/021; A61N 2005/109; G21G 4/02; G21G 4/20
(Continued)

(56) References Cited

U.S. PATENT DOCUMENTS 4,663,111 A * 5/1987 Kim ...................... C01B 3/0026
376/185
5,392,319 A * 2/1995 Eggers ..................... H05H 6/00
376/151
(Continued)

FOREIGN PATENT DOCUMENTS

EP    1 895 819 A1    3/2008
JP    2007-303983 A   11/2007
(Continued)

OTHER PUBLICATIONS

International Search Report dated Oct. 1, 2013 with English translation (six (6) pages).
(Continued)

*Primary Examiner* — Jack W Keith
*Assistant Examiner* — John T Nolan
(74) *Attorney, Agent, or Firm* — Crowell & Moring LLP

(57) ABSTRACT

Provided are a long-lived target for a neutron-generating device and a method for manufacturing the target therefore. The target is for a neutron-generating device and includes: a metal substrate retaining a target material; and a metal thin film for sealing that holds the target material at a retention surface X side. The retention surface X side of the metal substrate includes: a frame portion; and an embossed structure including: a plurality of island portions that are surrounded by the frame portion; and the rest recessed portion that is created by decreasing a thickness of a region other than the frame portion and the island portions by a thickness
(Continued)

of the target material. The metal thin film and surfaces of the frame portion and the island portions are subjected to hot isostearic pressing (HIP) bonding to seal the target material onto the recessed portion by using the metal thin film.

10 Claims, 14 Drawing Sheets

(51) Int. Cl.
*B23K 20/02* (2006.01)
*A61N 5/10* (2006.01)
*G21G 4/02* (2006.01)

(58) Field of Classification Search
USPC .......................................................... 376/151
See application file for complete search history.

(56) References Cited

U.S. PATENT DOCUMENTS

| 2010/0067638 A1* | 3/2010 | Zhuikov | B23K 20/023 |
| | | | 376/151 |
| 2010/0067640 A1 | 3/2010 | Willis et al. | |
| 2010/0195781 A1 | 8/2010 | Paul et al. | |
| 2013/0279638 A1* | 10/2013 | Matsumoto | G21G 4/02 |
| | | | 376/108 |

FOREIGN PATENT DOCUMENTS

| JP | 2008-22920 A | 2/2008 |
| JP | 2012-119062 A | 6/2012 |
| RU | 2 282 909 C2 | 8/2006 |
| WO | WO 2008/025737 A1 | 3/2008 |
| WO | WO 2012/073966 A1 | 6/2012 |

OTHER PUBLICATIONS

Japanese-language Written Opinion (PCT/ISA/237) dated Oct. 1, 2013 (six (6) pages).
European Search Report issued in counterpart European Application No. 13816649.1 dated Nov. 25, 2015 (thirteen (13) pages).
M. R. (Mac) Louthan, Jr., Aluminum-Lithium Technology and Savannah River's Contribution to Understanding Hydrogen Effects in Metals, Proceedings of the symposium 50 years of excellence in science and engineering at SRS, May 17, 2000, XP055228903, pp. 31-48.
Taiwanese Office Action issued in counterpart Taiwanese Application No. 10421194720 dated Sep. 3, 2015 (five (5) pages).
Russian-language Office Action issued in counterpart Russian Application No. 2015104869/07(007617) dated May 3, 2017 with English translation (15 pages).

* cited by examiner

TARGET FOR NEUTRON-GENERATING DEVICE AND MANUFACTURING METHOD THEREFOR

TECHNICAL FIELD

The present invention relates to a target for a neutron-generating device and a method for manufacturing the target that is irradiated with proton beams to generate neutrons.

BACKGROUND ART

A boron compound containing boron ($^{10}$B) is likely to accumulate in cancer cells, but is unlikely to accumulate in normal cells. In this boron compound, a $^{10}$B(n,α)$^7$Li reaction is utilized. That is, when boron ($^{10}$B) captures a thermal neutron or epidermal neutron, an a particle and a lithium atom ($^7$Li) are generated. Such an α particle and a lithium atom can selectively kill the cancer cells. This therapy has been known as boron neutron capture therapy. Conventionally, this boron neutron capture therapy has been carried out using a research reactor. However, the therapy schedule should be adjusted so as not to interfere with the operation schedule of the research reactor. Accordingly, it is not easy to make a therapy schedule. Also, problems have been caused in maintenance costs and a service life of the existing research reactor. In addition, in view of the cost and management, etc., it is markedly difficult to use a nuclear reactor as a neutron-generating device in regular hospitals.

Recently, much attention has been paid to neutron-generating devices in which protons are accelerated by an accelerator to have a predetermined energy level; and a given target material is then irradiated with the resulting protons to generate neutrons. Such neutron-generating devices are made as simple equipment when compared with nuclear reactors.

Generally speaking, target materials for these neutron-generating devices have been disclosed in Patent Literatures 1 and 2, and examples of the possible target materials include: lithium in which a $^7$Li(p,n)$^7$Be reaction can be utilized; beryllium in which a $^9$Be(p,n) reaction can be utilized; and solid heavy metals, such as uranium, tantalum, tungsten, lead, bismuth, and mercury, in which high-energy proton-and/or deuterium-mediated nuclear spoliation reactions are utilized.

In a neutron-generating device, high-energy protons and deuterium are accelerated by an accelerator; a solid heavy metal target material is irradiated with the resulting protons and deuterium; and a nuclear spoliation reaction is used to generate high-density neutrons. Unfortunately, the accelerator of this neutron-generating device is large and expensive, and the device is therefore difficult to be installed in regular hospitals.

In addition, the neutrons generated during the nuclear spoliation reaction have markedly higher energy levels. Consequently, a large-scale neutron irradiation unit is required, including: a target having a target material; a moderate that can moderate the energy levels of the neutrons to a predetermined energy level of thermal and epidermal neutrons used for boron neutron capture therapy; and a shield that prevents the high-energy neutrons from being leaked.

Here, Patent Literature 3 discloses that the energy threshold of a proton required for the $^7$Li(p,n)$^7$Be reaction is 1.889 MeV. Because of this, a proton accelerator can be small and relatively inexpensive. Thus, it has been proposed to use a metal lithium ($^7$Li) thin film as a target material that is irradiated with accelerated protons. The metal lithium, however, is highly reactive and easily reacts with oxygen, nitrogen, and/or moisture content in the air. In view of the above, the following target structure has been disclosed (see Patent Literature 3). A process such as vapor deposition is used to form a $^7$Li thin film at a thickness of several dozen μm on a metal substrate. A very thin stainless steel sheet is disposed on the thin film to seal the film onto the metal substrate. Also, this target includes coolant passages through which a coolant is made to circulate to cool the metal substrate holding the metal lithium.

PRIOR ART REFERENCE

Patent Literatures

Patent Literature 1: JP2008-22920A
Patent Literature 2: JP2007-303983A
Patent Literature 3: We2008/025737

Meanwhile, patients should not be irradiated with neutrons for a prolonged time during boron neutron capture therapy. Also, the levels of thermal and/or epidermal neutron flux that requires for irradiation on an affected tissue should be obtained. To achieve the above, for example, proton beams should have a current value of a predetermined level or higher.

In this regard, however, when a target retaining metal lithium is irradiated with proton beams from the stainless steel sheet side, the stainless steel sheet is heated and expanded. Once the stainless steel sheet is expanded and a contact between metal lithium and the stainless steel sheet is lost, the stainless steel sheet may not be cooled any more. Consequently, the stainless steel sheet may be broken and sealing of the metal lithium may be damaged.

In addition, even in the target structure disclosed in Patent Literature 3, melting of the metal lithium sealed using the stainless steel sheet is unavoidable because metal lithium has a relatively low melting point of 180° C. Accordingly, the stainless steel sheet may be expanded, so that the liquefied lithium is unevenly distributed at one portion of the metal substrate included in the target. As a result, the target may have markedly poor performance. Hence, the target has to be replaced by another expensive target before such a situation occurs.

SUMMARY OF THE INVENTION

Problems to be Solved by the Invention

The present invention has been developed to solve the above conventional problems. It is an object of the present invention to provide a long-lived target for a neutron-generating device and a method for manufacturing the target that has a simple structure and can maintain a function as a target even if metal lithium as a target material is progressively heated.

Means for Solving the Problems

In order to solve the above problems, an aspect of the present invention provides a target for a neutron-generating device that generates neutrons by using a $^7$Li(p,n)$^7$Be reaction while lithium as a target material is irradiated with proton beams accelerated by an accelerator. Herein, the target includes: a metal substrate that retains the target material; and a metal thin film for sealing that seals the target material onto the metal substrate at a retention surface side that holds the target material.

The metal substrate includes: on the retention surface side, an frame portion; and an embossed structure including: a plurality of island portions surrounded by the frame portion, the island portions having the same height as the frame portion; and the rest including a recessed portion that is created by decreasing a thickness of a region other than the frame portion and the island portions by a thickness of the target material.

Herein, the metal thin film for sealing is used to seal the target material onto the recessed portion of the metal substrate.

Preferably, the recessed portion of the embossed structure includes: a plurality of circular recessed portions that are hexagonally arranged inside the surrounding frame portion and are circular in a planar view; and communicating recessed portions in communication with the adjacent circular recessed portions.

Preferably, the bottom of the recessed portion has an attachment-promoting layer that causes the target material to better attach to the metal substrate.

Preferably, the metal substrate also includes a plurality of elongated coolant passages through which a coolant flows at a surface side opposite to the retention surface side.

Preferably, the metal substrate is made of iron or tantalum and the metal thin film for sealing is made of a stainless steel sheet, titanium sheet, titanium alloy sheet, beryllium sheet, or beryllium alloy sheet. Preferably, the attachment-promoting layer is a thin film layer made of copper, aluminum, magnesium, or zinc.

Preferably, in view of increasing an efficiency of generating neutrons, a material for the island portions of the embossed structure is a lithium alloy containing any of 1 to 20 mass % of Cu, 20 to 40 mass % of Al, and 45 to 60 mass % of Mg, and the remainder consisting of Li and unavoidable impurities.

According to an aspect of the present invention having the above features, the metal substrate includes: on the retention surface side holding the target material, an frame portion; and an embossed structure including: a plurality of island portions surrounded by the frame portion, the island portions having the same height as the frame portion; and the rest including a recessed portion that is created by decreasing a thickness of a region other than the frame portion and the island portions by a thickness of the target material. Herein, the metal thin film for sealing and surfaces of the frame portion and the island portions are subjected to, for example, HIP bonding; and the metal thin film for sealing is used to seal the target material onto the recessed portion of the metal substrate.

As a result, even if lithium of the target material is irradiated through the metal thin film with proton beams and the metal thin film is heated by the proton beams to be expanded, bonding the metal thin film to the surfaces of the island portions can prevent the metal thin film from being expanded and can maintain conditions in which the target material is tightly attached to the metal thin film.

Here, the metal substrate is cooled with a coolant, so that the metal thin film for sealing is also cooled by means of the metal substrate and lithium. This makes it possible to reduce probabilities of metal thin film damage due to excessive heat.

FIG. 7 illustrates a Comparative Embodiment where the metal thin film for sealing is attached only onto the frame portion. In this case, when the metal thin film for sealing is expanded, the expansion volume tends to be larger around the center of the frame portion. As a result, when metal lithium as a target material is irradiated with proton beams and is heated and melted, the metal lithium is dislocated to a lower portion between the metal substrate and the metal thin film of the target. Accordingly, almost no metal lithium may be present in the site of the irradiation with the proton beams.

According to an aspect of the present invention, the metal thin film for sealing and the surfaces of the frame portion and the island portions are subjected to HIP bonding, and the metal thin film is bonded to the retention surface side of the metal substrate. Meanwhile, irradiation with proton beams may cause metal lithium sealed within the recessed portion to be heated and melted. Even in this case, a change in the thickness of the target material, caused by the expansion of the metal thin film for sealing, may be small. Hereby, metal lithium can be evenly distributed inside the surrounding target frame portion between the metal substrate and the metal thin film for sealing.

Consequently, the target may have an extended service life, so that a cumulative irradiation time of proton beams can be extended until the target is replaced by another expensive target. That is, this helps reduce treatment costs paid by patients who receive boron neutron capture therapy.

In addition, another aspect of the present invention provides a target for a neutron-generating device that generates neutrons by using a $^7Li(p,n)^7Be$ reaction while lithium as a target material is irradiated with proton beams accelerated by an accelerator. The target includes: a metal substrate that retains the target material; and a metal thin film for sealing that seals the target material onto the metal substrate at a retention surface side that holds the target material. Herein, the target material is a lithium alloy containing any of 1 to 20 mass % of Cu, 20 to 40 mass % of Al, and 45 to 60 mass % of Mg, and the remainder consisting of Li and unavoidable impurities.

According to this aspect of the present invention having the above features, a melting point of the target material is several hundred degrees higher than a relatively low melting point of pure metal lithium as a target material. This may result in preventing the target material from being melted by heat due to the irradiation with the proton beams. Further, this can also prevent the melted target material from being unevenly distributed at one portion of the metal substrate, thereby preventing target performance from being deteriorated.

Effect of the Invention

The present invention can provide a long-lived target for a neutron-generating device and a method for manufacturing the target that has a simple structure and can maintain a function as a target even if metal lithium as a target material is progressively heated.

BRIEF DESCRIPTION OF THE DRAWINGS

FIG. 6A illustrates a method including: an embossed structure processing step of producing an embossed structure on the retention surface X side (i.e., a front surface side) of a metal substrate 52A of the target 51A; a coolant passage creating step of producing grooves for coolant passages 52d at the side (i.e., a back surface side) opposite to the retention surface of the metal substrate, and thereafter; an attachment-promoting layer formation step of producing an attachment-promoting layer at the bottom of a recessed portion 52c, and thereafter; and a target material filling step of filling the recessed portion 52c with a melted target material in vacuo or under an argon gas atmosphere.
FIG. 6B illustrates a condition after the target material filling step.
FIG. 6C illustrates a condition after a retention surface smoothing step.
FIG. 6D illustrates a condition after a bonding step of subjecting to HIP bonding a blackboard 55, a metal thin film 53 for sealing, and the metal substrate 52A obtained by the last target material filling step.

FIG. 7A is a perspective view of the target 51B. FIG. 7B is a cross-sectional view taken along the line Y-Y in FIG. 7A.

FIG. 8A is a schematic perspective view. FIG. 8B is a cross-sectional view taken along the line Z-Z in FIG. 8A.

FIG. 11A is an exploded view illustrating the target 51D. FIG. 11B is a plan view showing a metal substrate 52D holding a target material 54. FIG. 11C is an enlarged perspective view showing an embossed structure on the metal substrate 52D.

FIG. 12A is an exploded view illustrating the target 51E. FIG. 12B is a plan view showing a metal substrate 52E holding a target material 54.

FIG. 13A illustrates a method including: a thickness-decreasing step of producing a recessed portion 52c by uniformly reducing the thickness of a metal substrate 52E0 of the target 51E at the retention surface X side (a front surface side); a coolant passage creating step of producing grooves for coolant passages 52d at the side (a back surface side) opposite to the retention surface of the metal substrate 52E0, and thereafter; an attachment-promoting layer formation step of producing an attachment-promoting layer at the bottom of the recessed portion 52c, and thereafter; and a lithium alloy filling step of filling the recessed portion 52c with a melted lithium alloy 54a in vacuo or under an argon gas atmosphere. FIG. 13B illustrates a condition after the lithium alloy filling step, followed by a retention surface smoothing step. FIG. 13C illustrates a condition after an embossed structure processing step. FIG. 13D illustrates another target material filling step of filling the recessed portion 52c with a melted target material 54 in vacuo or under an argon gas atmosphere. FIG. 13E illustrates a condition after the target material filling step, followed by another retention surface smoothing step.

EMBODIMENTS FOR CARRYING OUT THE INVENTION

The following describes a neutron-generating device 100 for boron neutron capture therapy (BNCT) by referring to FIGS. 1 to 4. The device 100 uses a target for a neutron-generating device according to an embodiment of the present invention.

Figure 1:
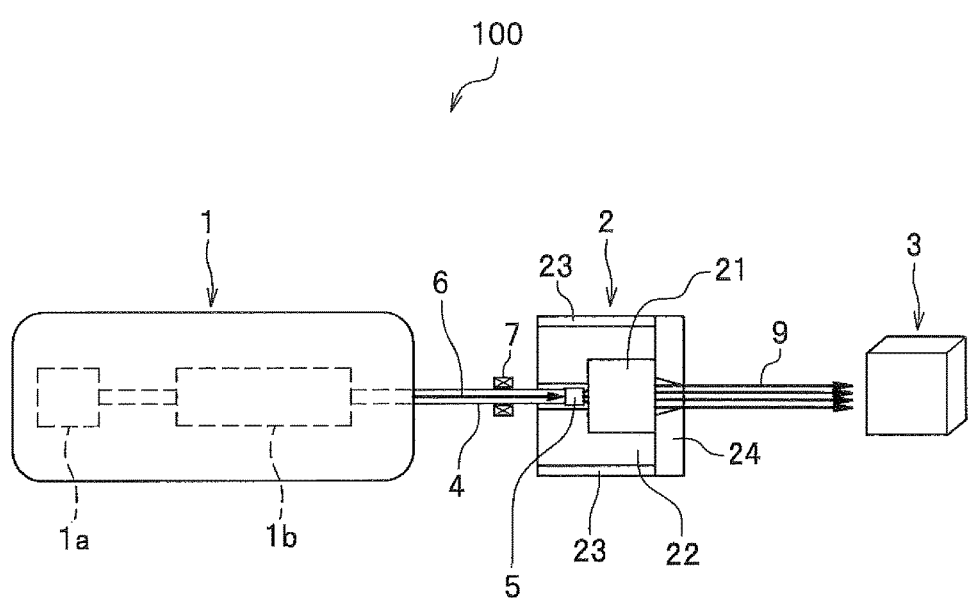
FIG. 1 outlines a whole neutron-generating device.

FIG. 1 outlines a whole neutron-generating device.

As shown in FIG. 1, the neutron-generating device 100 primarily includes: a proton beam-generating unit 1; a beam conduit 4 that guides vacuum proton beams 6 generated in the proton-beam-generating unit 1 to a target section 5; and an irradiation unit 2 that produces neutron beams 9 to irradiate a patient's affected tissue (i.e., a treatment unit 3) with the neutron beams 9 while decreasing energy levels of neutrons generated in the target section 5 irradiated with the proton beams 6 to a predetermined energy level.

(Proton Beam-generating Unit 1)

The proton beam-generating unit 1 includes: an ion source 1a that generates a predetermined amount of protons (i.e., hydrogen ion); and an accelerator 1b that accelerates the protons.

The neutron-generating device 100 according to this embodiment is used for BNCT. Metal lithium is used as a target material of its target section 5. The target material is then irradiated with protons and a $^7Li(p,n)^7Be$ reaction is utilized to generate neutrons. Here, the accelerator 1b is used to be able to variably set a proton energy range to be from 1.889 MeV, which is a threshold of the $^7Li(p,n)^7Be$ reaction occurring in the target material, to 3.0 MeV. Then, a current value of the proton beams 6 may be about 15 to 20 MA while a patient's treatment period for neutron irradiation should be not so long and be intended to last, for example, about 30 min.

As a target level of epidermal neutrons of the neutron beams 9 with which a patient is irradiated from the irradiation unit 2, neutron flux has a level of $2\times10^9$ n/cm$^2$s at a position 2.5 cm deep from the body surface.

The proton beam-generating unit 1 should satisfy such a required specification and may be small and inexpensive. The proton beam-generating unit 1 may employ an EcR (Electron Cyclotron Resonance) ion source as the ion source 1a and an electrostatic accelerator as the accelerator 1b.

In the ion source 1a, electron cyclotron resonance is herein used to generate hydrogen ($^1H$) plasma; a solenoid coil or a permanent magnet and sextuple permanent magnet are used to confine the hydrogen ($^1H$) plasma; and the ion source 1a then generates hydrogen ions ($^1H+$). The ECR ion source can stably and continuously perform electrode less discharge for a long period and is characterized in that the ECR ion source can generate high-intensity ion beams.

The electrostatic accelerator is a device in which high voltage direct current is applied between electrodes and a potential difference between the electrodes is used to accelerate charged particles. An accelerator according to this embodiment can output low-energy continuous ion beams at a relatively high current level. Examples of the accelerator used include a Dynamiter (a registered trademark of Ion Beam Applications S.A. (IBA Inc.), Belgium) (see JP2012-500454A). This accelerator 1b is highly likely to produce proton beams 6 at a current level of 15 to 20 mA. The proton beams 6 as obtained by this accelerator 1b may have an energy level of from about 1.889 to 3.0 MeV.

As shown in FIG. 1, a beam-condensing lens 7 is installed partway through the beam conduit 4 (i.e., at the left side in FIG. 1) before the irradiation unit 2. When a target material 54 (see FIG. 4) of the target section 5 is irradiated with the proton beams 6, the proton beams 6 may spread inside the beam conduit 4 and collide with the inner wall of the beam conduit 4, so that the intensity of the proton beams 6 may decrease. The beam-condensing lens 7 is to prevent this decrease. As the beam-condensing lens 7, a combination of quadruple electromagnets, whose polarity is reversed in the proton beam 6 direction, is generally used. An end portion of the beam conduit 4 has a collimator 10 attached to the target section 5. The collimator 10 adjusts how the proton beams spread in vertical and lateral directions.

The collimator 10 focuses the proton beams 6 traveling to the target section 5 on a region positioned in the target material 54 of the target section 5. The collimator 10 has, for example, a cylindrical inner wall and has a water-cooled jacket (not shown) outside of its inner wall to cool the inner wall.

In addition, as shown in FIG. 1, the proton beam-generating unit 1 and the beam-condensing lens 7 are linearly arranged on the beam conduit 4, and nothing else is presently disposed therebetween. As disclosed in JP2008-22920A, however, a rotary gantry may be deployed in such a manner that the irradiation unit 2 can irradiate an affected tissue in the treatment unit 3 with neutron beams 9 from an appropriate direction. The gantry portion includes a plurality of deflection electromagnets that can deflect the proton beams 6 in a certain direction. After the deflection electromagnets, the beam-condensing lens 7 may be disposed. In this case, it is convenient to have a rotating seal member on a part of the beam conduit 4. The proton beams 6 are bent at the part.

(Irradiation Unit 2)

The appearance of the irradiation unit 2 is substantially cylindrical in an incident direction of the proton beams 6. A cylindrical moderate 21 is disposed at the forward side of the target section 5. A reflector 22 covers the circumference and the rear side (i.e., in a direction opposite to the incoming direction of the proton beams 6). The beam conduit 4 penetrates through a through hole disposed in a center portion of the reflector 22. The circumference of the reflector 22 has a cylindrical neutron absorber 23 so as to shield radiation.

A filter (not shown) is disposed at the forward side (i.e., irradiation side) of the moderate 21 and the reflector 22. Further, a collimator 24 having an opening at its center portion is disposed at the further forward side.

Examples of a material for the moderate 21 used include magnesium fluoride ($MgF_2$) and aluminum fluoride ($AlF_3$). Examples of a material for reflector 22 include graphite (C) and lead (Pb). In this regard, however, when lead is used for the reflector 22, the irradiation unit 2 may be heavy. Aside from this disadvantage, lead can exert an effect of shielding γ rays generated in the target section 5. When the above is taken into consideration, lead is more preferable than graphite.

As for the neutron absorber 23, used is a material without emitting γ rays during neutron absorption while fast neutrons are theorized by, for example, hydrogen. Examples of the material include boron-containing polyethylene resins.

The above filter is made of a material having a function of shielding neutrons and transmission γ rays. Examples of the material used include lead fluoride ($PbF_2$) and bismuth that can prevent γ rays harmful to treatment, such as γ rays generated during nuclear reactions at the target section 5 and γ rays generated during neutron moderation processes, and through which epidermal neutrons can penetrate and can be used to irradiate a treatment tissue. When lead fluoride and bismuth are compared, bismuth is a material with higher neutron penetration and γ ray-shielding performance. However, bismuth is a very expensive material. In view of the above, lead fluoride or bismuth may be selectively used depending on their price and required performance.

A material for the collimator 24 may be, for example, lithium fluoride (LiF), which has increased neutron shielding performance and decreased γ ray generation caused by neutron irradiation.

(Target Section 5)

Figure 2:
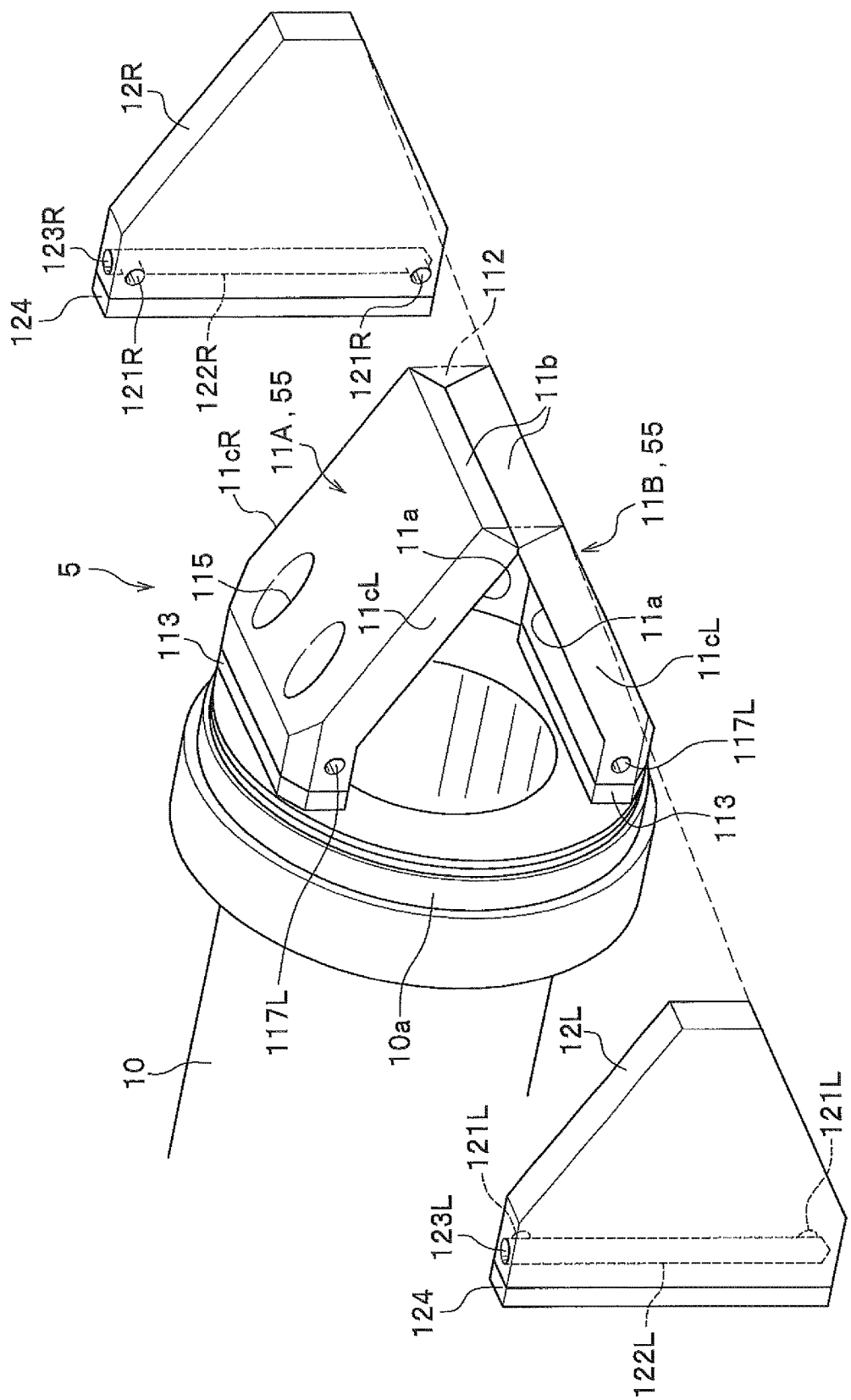
FIG. 2 outlines a target section.

The following illustrates the structure of the target section 5 by referring to FIGS. 2 to 6D. FIG. 2 outlines the target section.

Figure 3:
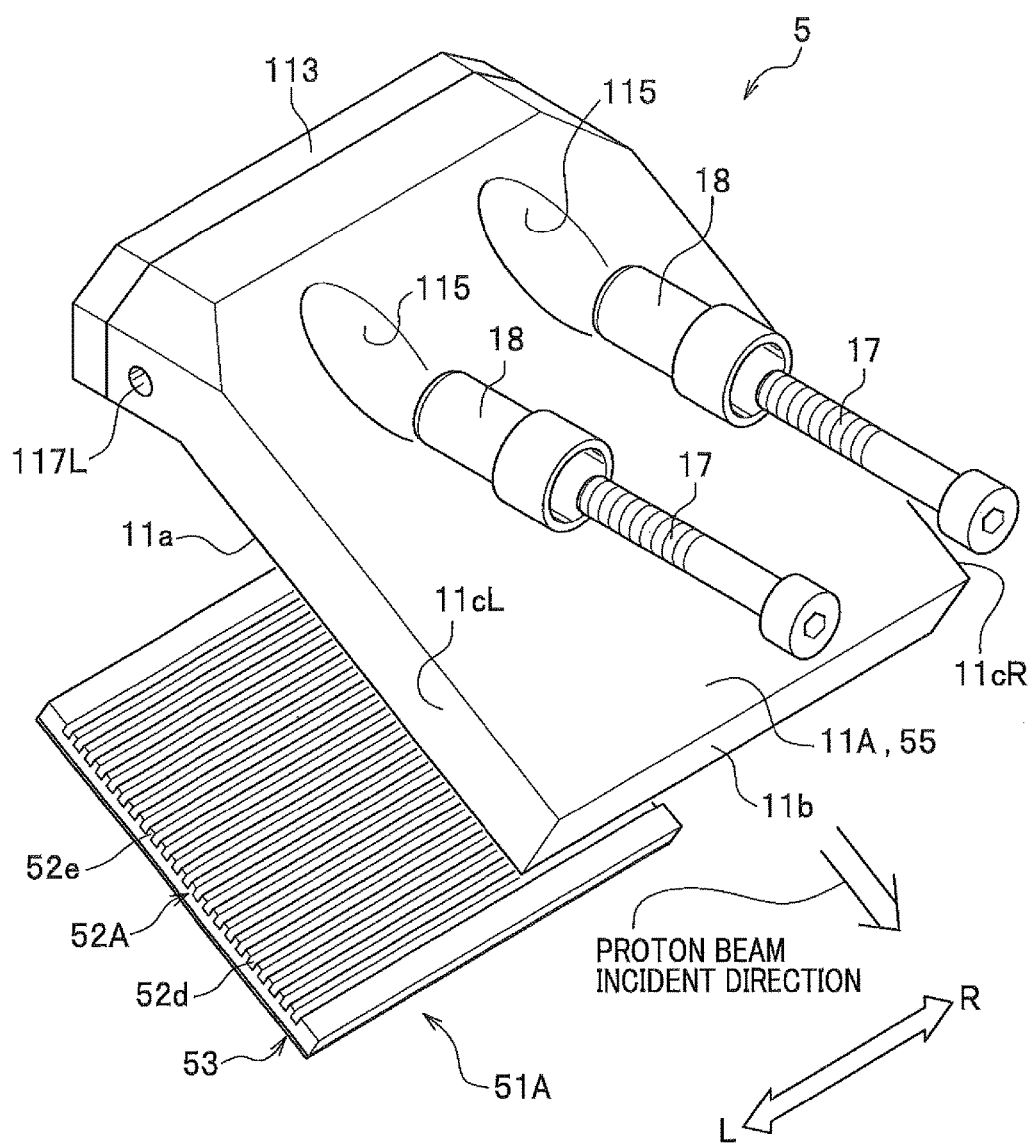
FIG. 3 illustrates a mounting structure of a target panel.

FIGS. 2 and 3 illustrate the target section 5 as follows: two target panels 11A and 11B are used; an end surface 11b of each target panel is joined like a V-shape at their end side (i.e., at a side through which the proton beams 6 travel); each target panel is inclined in respect to the incident direction of the proton beams 6 by, for example, 30 degrees; and each target panel is attached via an electrical insulator 113 to a tip flange part 10a of the collimator 10 installed at the end portion of the beam conduit 4. Further, as shown in FIG. 2, left and right side plates 12L and 12R are each water tightly attached via an electrical insulator 124 to panel side surfaces 11cL and 11cR of the target panels 11A and 11B, respectively. Also, the side plates 12L and 12R are in contact with the tip flange part 10a.

Figure 5:
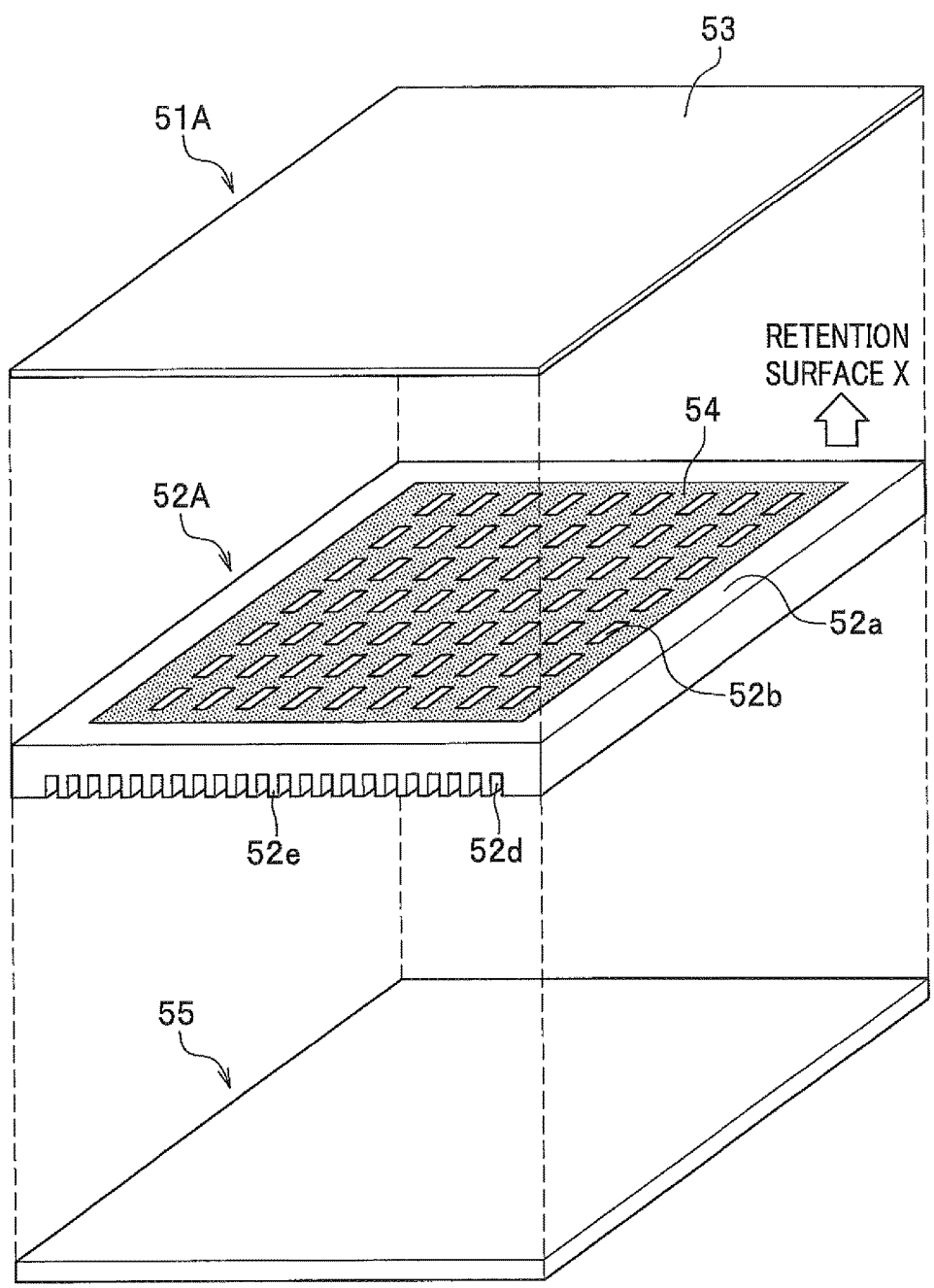
FIG. 5 is an exploded view illustrating a target.

Then, a capped cylindrical casing (not shown in FIG. 2) is mounted via a seal member, for example, using screws to the tip flange part 10a from its outside so as to keep the inside of the casing airtight (see FIG. 5 of Patent Literature 3).

In addition, the end surfaces 11b are fixed, for example, using screws to a beam stopper 112 so as to prevent the proton beams 6 from passing through the unit as depicted using the imaginary line (two-dot chain line). The beam stopper 112 is a structure to stop the proton beams 6 so as not to irradiate the casing when the proton beams 6 travel through a gap between the end surfaces 11b. Examples of a material used for the beam stopper 112 include low-carbon steel.

The target panels 11A and 11B shown in FIG. 2 respectively have coolant passage holes 117L at their left side. In addition, the target panels 11A and 11B respectively have coolant passage holes 117R at their right side.

The coolant passage holes 117 L correspond to the upper and lower coolant passage holes 121L of the side plate 12L. While a watertight sealing material (not shown) is used to prevent leakage of a coolant, the coolant can pass through a coolant channel 122L to an upper coolant passage hole 123L.

Inside of the above casing (not shown), a first coolant pipe (not shown) is used to connect the coolant passage hole 123L and a first coolant passage hole (not shown) positioned at the tip flange part 10a. The first coolant pipe includes: for example, a resin pipe resistant to neutron irradiation; and watertight metal connectors at both ends. The first metal connector of the first coolant pipe is connected to the first coolant passage hole, and the coolant is distributed using the coolant passage of the collimator 10 (see FIG. 5 of Patent Literature 3). The second metal connector of the first coolant pipe is connected to the coolant passage hole 123L.

Likewise, the coolant passage holes 117R (not shown in FIG. 2) each correspond to the upper and lower coolant passage holes 121R of the side plate 12R. While a watertight sealing material (not shown) is used to prevent leakage of the coolant, the coolant can pass through a coolant channel 122R to an upper coolant passage hole 123R.

Inside of the above casing (not shown), a second coolant pipe (not shown) is used to connect the coolant passage hole 123R and a second coolant passage hole (not shown) positioned at the tip flange part 10a. The second coolant pipe has the same structure as of the first coolant pipe. The first metal connector of the second coolant pipe is connected to the second coolant passage hole, and the coolant is distributed using the coolant passage of the collimator 10 (see FIG. 5 of Patent Literature 3). The second metal connector of the second coolant pipe is connected to the coolant passage hole 123R. In this way, one of the first and second coolant pipes may supply the coolant to the target panels 11A and 11B. The other one of the first and second coolant pipes may discharge the coolant from the target panels 11A and 11B through the coolant passage of the collimator 10.

As used herein, examples of the coolant used include pure water.

Figure 4:
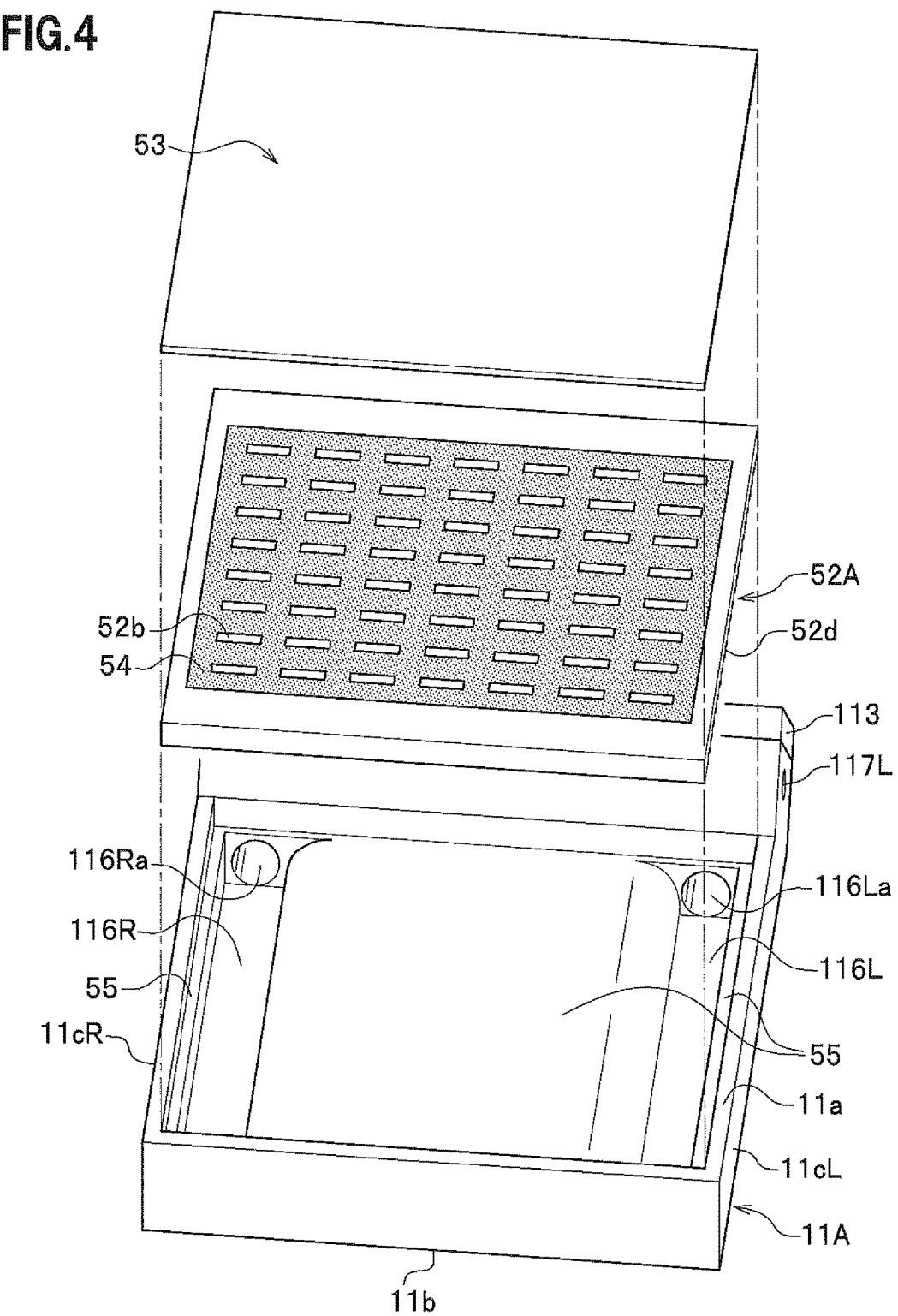
FIG. 4 is an exploded view illustrating the structure of a target panel when viewed from the beam irradiation surface 11a side.

FIG. 3 illustrates a mounting structure of the target panel. FIG. 4 is an exploded view illustrating the structure of the target panel 11A when viewed from the beam irradiation surface 11a side. FIG. 3 illustrates, as an example, the target panel 11A in FIG. 2. Here, the target panel 11B has the same mounting structure.

A mounting bolt 17 is inserted through an insertion hole 115 and is screwed via an electrical insulation piece 18 into a female screw hole (not shown) positioned at the end surface of the tip flange part 10a. Then, a prefabricated assembly including the target panels 11A and 11B and the side plates 12L and 12R is mounted on the tip flange part 10a. Because the insulation piece 18 is interposed, the mounting bolt 17 contacts neither the target panel 11A nor 11B.

Before the target panels 11A and 11B have been attached, the targets 51A should be mounted on the beam irradiation surfaces 11a of the target panels 11A and 11B, which surfaces are the side (front side) irradiated with the proton beams 6. However, the target panel and the target are separated for description clarity in FIG. 3. Meanwhile, as described below in the description of FIG. 5, the target 51A includes: a metal substrate 52A; a target material 54 (see FIGS. 4 and 5); a metal thin film 53 for sealing; and a blackboard 55. As used herein, the blackboard 55 is part of each of the target panels 11A and 11B (see FIG. 4). In this connection, examples of a material for the target panels 11A and 11B include carbon steel and copper.

Types of a component member for the metal thin film 53 should be used to prevent a chemical reaction such as oxidation of the target material 54. Also, the metal thin film 53 should not be easily corroded by the target material 54. In addition, neither the proton beams 6 should be attenuated nor excessive heat should be generated when the metal thin film 53 is irradiated with the proton beams 6. In view of the above requirement, it is preferable to select the types of the component member through which the proton beams 6 pass easily. Specific examples of the suitable component member for the metal thin film 53 include a stainless steel sheet, titanium sheet, titanium alloy sheet, beryllium sheet, and beryllium alloy sheet. In view of low production cost, a stainless foil at a thickness of 4 µm is herein used for the metal thin film 53 for sealing as an example. When a titanium alloy sheet is used, the sheet preferably has a thickness of 5 µm. When a beryllium alloy sheet is used, the sheet preferably has a thickness of 10 µm.

The back surface of the metal substrate 52A has grooved coolant passages 52d as shown in FIGS. 3, 4, and 5. The back surface of the metal substrate 52A is attached to the blackboard 55 at the beam irradiation surface 11a of the target panel 11A as shown in FIG. 4. The blackboard 55 has a recess part that is a little step holding the beam irradiation surface 11a. In FIG. 4, the target panel 11A is viewed from the backside, so that the left-right direction is reversed. The left and right side portions of the blackboard 55 include concave manifolds 116L and 116R used to provide the coolant passages 52d with the coolant and to recover the coolant from the coolant passages 52d. A coolant passage hole 116La that is an opening for the manifold 116L is in communication with the coolant passage hole 117L. Likewise, a coolant passage hole 116Ra that is an opening for the manifold 116R is in communication with the coolant passage hole 117R.

The same structure is used for the target panel 11B. In this regard, however, the reference signs denoting the left-right direction in FIG. 4 are changed. Nevertheless, the shape thereof is identical.

FIG. 5 is an exploded view illustrating the target. FIG. 5 provides a simplified schematic view of the blackboard 55 as a plate. Like the blackboard 55 of the target panel 11A (11B) shown in FIG. 4, this blackboard also includes the manifolds 116L and 116R that are concave elongated grooves.

Figure 6A:
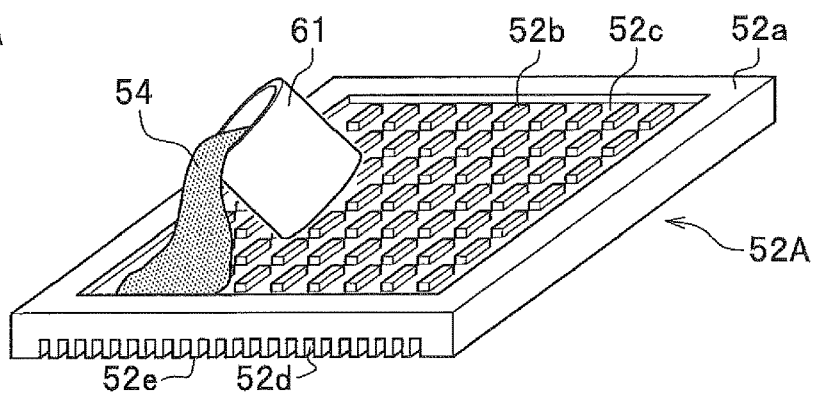
FIGS. 6A-6D illustrate a method for manufacturing a target 51A.

As shown in FIG. 5, the front surface side (referred to as the "retention surface X" in FIG. 5) of the substantially rectangular metal substrate 52A includes: a circumferential frame portion 52a; discrete island portions 52b that are surrounded by the frame portion 52a and are regularly arranged in the lateral and longitudinal directions as shown in FIG. 6A; and the rest recessed portion 52c where the thickness is decreased. The surface height of the frame portion 52a is equal to the surface height of each island portion 52b. The step height of the recessed portion 52c is equal to the thickness of the target material metal lithium (Li) and is, for example, 50 µm. The structure of these island portions 52b with the rest recessed portion 52c is what is called an "embossed structure". The structure can be processed using, for example, milling, electric discharge machining, and/or chemical etching.

The back surface side (i.e., the surface opposite to the retention surface X) of the metal substrate 52A includes: grooved coolant passages 52d; and the rest cooling fins 52e.

Then, this recessed portion 52c is filled with metal lithium. After that, the back surface of the metal substrate 52A is placed on the blackboard 55 as shown in FIG. 4. Further, the metal thin film 53 for sealing is placed on the retention surface X of the metal substrate 52A. Subsequently, HIP bonding is used to attach the metal thin film 53 to the surface of the frame portion 52a and the surfaces of the island portions 52b. At the same time, the blackboard 55 is bonded to the back surface of the metal substrate 52A.

Here, the target material metal lithium (Li) has a thickness of 50 µm. The target panels 11A and 11B are inclined by 30 degrees with respect to the irradiation direction of the proton beams 6. Thus, the travel distance of the proton beams 6 passing through the target material 54 is about 110 µm, which is a sufficient thickness. For example, the energy level of the proton beams 6 is decreased from 2.8 MeV to less than 1.889 MeV while the proton beams 6 travel the distance through the metal lithium (i.e., the target material 54). Then, the protons penetrate into the metal substrate 52A. Accordingly, this can prevent γ ray emission caused by inelastic scattering between lithium and the incident protons.

Examples of a preferable material for the metal substrate 52A include low-carbon steel (Fe) and tantalum (Ta). The thickness from the bottom of the recessed portion 52c to the groove bottom of the coolant passage 52d is a thickness at which all the rest protons passing through the target material 54 irradiated with the proton beams 6 can be blocked.

Iron, like tantalum (Ta), is highly resistant to hydrogen embracement and blistering due to a lattice defect caused by proton collisions, and is a low cost material. In view of heat conductivity, copper (Cu) is preferable as a material for the target panels 11A and 11B. The metal substrate 52A may be attached using HIP (Hot Isostearic Pressing) bonding. When this is taken into account, carbon steel may be suitable.

(Method for Manufacturing Target 51A)

Figure 6B:
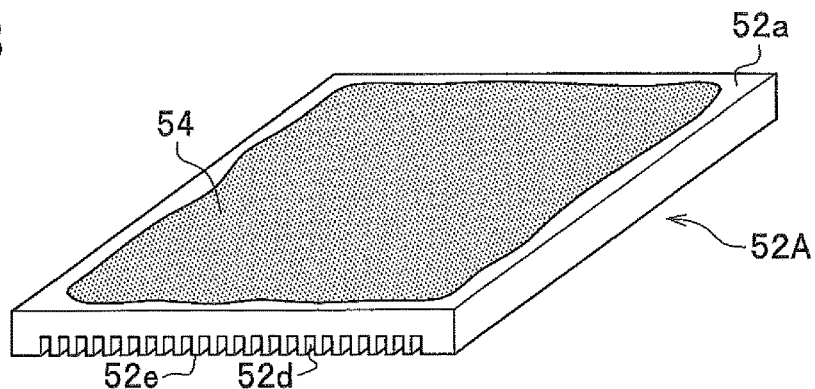
Figure 6C:
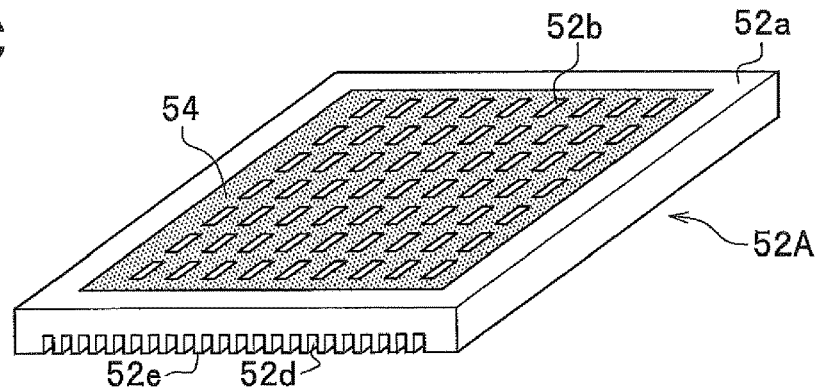
Figure 6D:
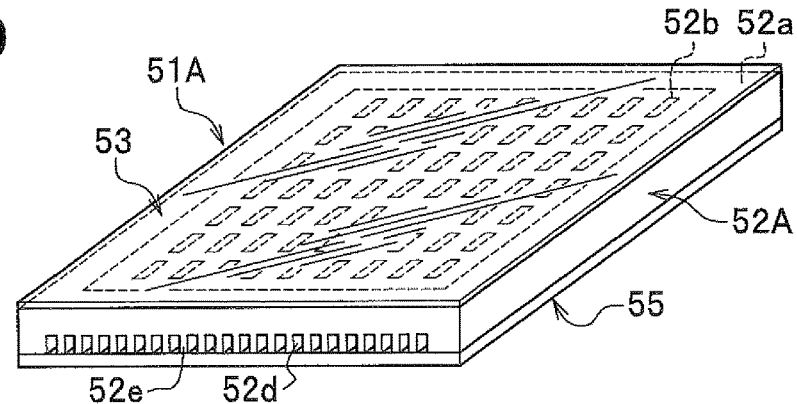

Next, a method for manufacturing the target 51A will be explained by referring to FIGS. 6A-6D. FIGS. 6A-6D illustrate how to manufacture the target 51A. FIG. 6A illustrates a method including: an embossed structure processing step of producing an embossed structure on the retention surface X side (a front surface side) of the metal substrate 52A of the target 51A; a coolant passage creating step of producing grooves for coolant passages 52d at the side (i.e., a back surface side) opposite to the retention surface of the metal substrate, and thereafter; an attachment-promoting layer formation step of producing an attachment-promoting layer at a bottom of the recessed portion 52c, and thereafter; and a target material filling step of filling the recessed portion 52c with a melted target material in vacuo or under an argon gas atmosphere. FIG. 6B illustrates a condition after the target material filling step. FIG. 6C illustrates a condition after a retention surface smoothing step. FIG. 6D illustrates a condition after a bonding step of subjecting to HIP bonding the blackboard 55, the metal thin film 53 for sealing, and the metal substrate 52A obtained by the last target material filling step.

The target 51A is manufactured as follows.

(1) Coolant Passage Formation Step

The original metal substrate 52A is a rectangular low-carbon steel or tantalum plate. In order to form the coolant passages 52d, many grooves are created using, for example, milling on one surface (i.e., the back side (corresponding to the lower surface in FIG. 6A)) of the metal substrate to produce cooling fins 52e (see FIG. 6A).

(2) Embossed Structure Processing Step

The front surface side (i.e., corresponding to the upper surface side in FIG. 6A) of the metal substrate 52A includes: the frame portion 52a; and the discrete island portions 52b that are surrounded by the frame portion 52a and are regularly arranged in the lateral and longitudinal directions as shown in FIG. 6A. The rest recessed portion 52c is created by decreasing the thickness by a predetermined length. For example, the thickness is decreased using milling by 50 μm, which is the same thickness as of the target material metal lithium (Li).

(3) Attachment-promoting Layer Formation Step

After the embossed structure processing step, a very thin layer (i.e., attachment-promoting layer) made of copper, aluminum, magnesium, or zinc is deposited using a film formation process such as vapor deposition and sputtering on the bottom of the recessed portion 52c. The thickness of the layer is, for example, 0.05 μm. This process makes better the attachment (or wearability) between the metal substrate 52A and lithium that is the target material 54. At this time, before the film formation process such as vapor deposition and sputtering, the upper surfaces (in FIG. 6A) of the frame portion 52a and the island portions 52b are masked so as not to form a copper thin layer. After the film formation process such as vapor deposition and sputtering, the mask is ripped off.

(4) Target Material Filling Step

Next, molten metal lithium that is the target material 54 contained in a crucible 61 is poured in vacuo or under an argon gas atmosphere into the recessed portion 52c (see FIGS. 6A and 6B). Because argon gas contains oxygen and moisture content ($H_2O$) as impurities, the molten metal lithium may be oxidized. Hence, it is preferable to fill the recessed portion 52c with the metal lithium in vacuo.

(5) Retention Surface Smoothing Step

The metal lithium that is the target material 54 used to fill the recessed portion 52c during the target material filling step (4) is solidified as it is in vacuo or under an argon gas atmosphere. However, as shown in FIG. 6B, the metal lithium is also attached onto the surfaces of the frame portion 52a and the island portions 52b, and the level of the metal lithium is higher than the surfaces of the frame portion 52a and the island portions 52b.

Then, the metal lithium is ground and leveled using, for example, milling in vacuo or under an argon gas atmosphere to the height of the surfaces of the frame portion 52a and the island portions 52b. The resulting metal lithium powder is also removed by blowing with argon gas. As a result, the surfaces of the frame portion 52a and the island portions 52b are exposed and kept clean. This makes only the recessed portion 52c filled with the metal lithium (see FIG. 6C). Because argon gas contains oxygen and moisture content ($H_2O$) as impurities, the molten metal lithium may be oxidized. Hence, it is preferable to grind the metal lithium in vacuo.

(6) Bonding Step

First, the blackboard 55 (e.g., the blackboard 55 is schematically depicted as a rectangular plate for illustration purpose in FIG. 6D) for the target panel 11A (or the target panel 11B) is horizontally placed under an argon gas atmosphere. Next, the back side of the metal substrate 52A is placed on the blackboard 55. Then, the metal thin film 53 for sealing is placed on the retention surface X (see FIG. 5) of the metal substrate 52A.

After that, an abutting member that is not bonded to the metal thin film 53 during HIP bonding and that has a flat abutting surface facing the metal thin film 53 is placed on the metal thin film 53. Examples of a material for the abutting member include ceramics.

This abutting member has a suitable weight and is to exclude argon gas between the metal thin film 53 and the retention surface X of the metal substrate 52A before the initiation of the HIP bonding. Also, the abutting member makes it possible to keep the flat metal thin film 53 in contact with the retention surface X of the metal substrate 52A during the HIP bonding. This can prevent the metal thin film 53 from being indented into the recessed portion 52c when the metal lithium is melted.

Thereafter, the HIP bonding is carried out. According to this bonding step, the metal thin film 53 can be bonded to the surfaces of the frame portion 52a and the island portions 52b of the metal substrate 52A while the blackboard 55 is bonded to the metal substrate 52A.

At this time, not only the blackboard 55 is bonded to the lower surfaces of the cooling fins 52e of the metal substrate 52A, but also the corner side portions of the metal substrate 52A are bonded to the frame portion of the blackboard 55 at the beam irradiation surface 11a side of the target panel 11A (or the target panel 11B). Consequently, the manifolds 116L and 116R are water tightly attached at the beam irradiation surface 11a side of the target panel 11A (or the target panel 11B).

This bonding step can reduce the number of steps when compared with the bonding step in which the bonding of the metal thin film 53 to the surfaces of the frame portion 52a and the island portions 52b of the metal substrate 52A and the bonding of the blackboard 55 to the metal substrate 52A are separately performed.

Then, the above method is used to complete the target 51A.

Figure 7A:
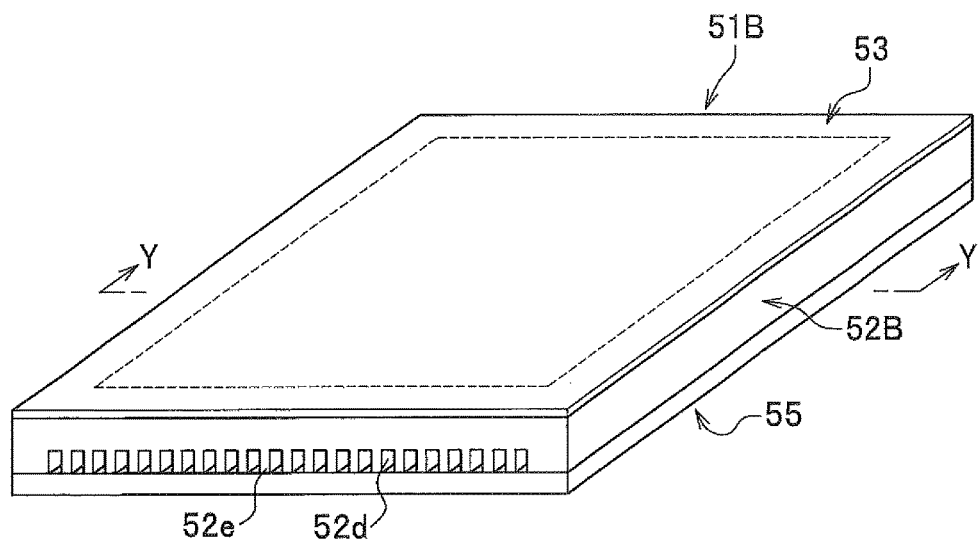
FIGS. 7A-7B illustrate the structure of a target 51B according to a comparative embodiment.
Figure 7B:
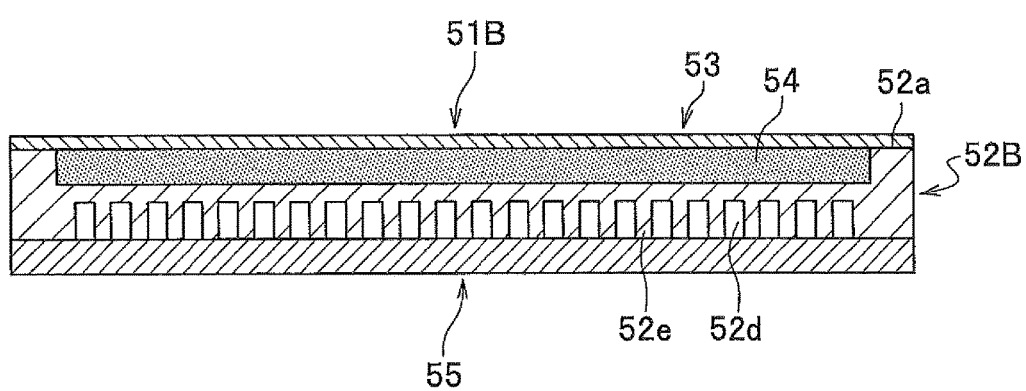

FIGS. 7A and 7B illustrate the structure of a target 51B according to a comparative embodiment. FIG. 7A is a perspective view of the target 51B. FIG. 7B is a cross-sectional view taken along the line Y-Y in FIG. 7A.

In the target 51B according to the comparative embodiment, the structure of the front surface side of the metal substrate 52B includes: the circumferential frame portion 52a; and a recessed portion 52c that is surrounded by the frame portion 52a and that is uniformly concave. This recessed portion 52c without an embossed structure is tightly filled with pure metal lithium that is the target material 54.

In contrast, according to the target 51A of the present embodiment, the surfaces of the frame portion 52a and the island portions 52b of the metal substrate 52A are bonded to the metal thin film 53 on the metal substrate 52A at the side of the retention surface X irradiated with the proton beams 6. However, according to the comparative embodiment, the metal substrate 52B has no embossed structure at the side of the retention surface X irradiated with the proton beams 6. Thus, when comparing the present embodiment having the embossed structure to the comparative embodiment having no embossed structure, even if the target material 54 metal lithium is heated by the proton beams 6 and becomes melted, the present embodiment can suppress thermal expansion of the metal thin film 53. Further, the present embodiment can prevent occurrence of gravity-mediated dislocation of the molten metal lithium to one side of the plane inside the frame portion 52a.

In addition, according to the present embodiment, the collimator 10 is used to collimate the proton beams 6 so as to uniformly irradiate the target materials 54 of the target panels 11A and 11B with the proton beams 6. This configuration helps prevent only part (a spot) of the metal thin film 53 on the target 51A from being irradiated with the proton beams 6. Accordingly, heat damage of the metal thin film 53 can be avoided. This results in a prolonged period until the metal thin film 53 for sealing reaches the end of its service life. Hence, the service life of the target 51A may be extended.

By contrast, in the comparative embodiment, the collimator 10 may be used to uniformly irradiate the target material 54 of the target 51B with the proton beams 6. This case, however, results in the gravity-mediated dislocation of the molten metal lithium to one side of the plane inside the frame portion 52a. Consequently, a portion without contacting the molten metal lithium appears at the back side of the metal thin film 53 for sealing. This portion is not cooled with the molten metal lithium. Also, a time until the metal thin film 53 is damaged by excessive heat is shortened. Hence, the service life of the target 51B may be shortened.

By contrast, the target 51A according to the present embodiment does not experience such a situation. Thus, the target 51A has a longer service life than the target 51B according to the comparative embodiment. Overall, the target 51A helps reduce cost per patient of boron capture therapy.

In addition, the metal lithium of the target material 54 has a thickness of 50 μm. This can prevent the energy of the proton beams 6 from being lost in the metal lithium due to inelastic scattering between the lithium and the proton beams 6. Accordingly, the above can decrease occurrence of inelastic scattering γ rays. Consequently, the γ ray-shielding structure of the irradiation unit 2 can be made to weigh less and the irradiation unit 2 can be made compact.

Further, the molten metal lithium of the target material 54 may circulate through the target section 5 of the irradiation unit 2. In this case, the structure of the circulation pipe may be complex. At the same time, the circulation pipe disposed outside the irradiation unit 2 requires a α-ray-shielding structure. The present embodiment does not require such a structure and the target section 5 can be made compact.

In this regard, however, examples of a material for the metal substrate 52A include low-carbon steel and tantalum. This material can prevent blistering due to proton (hydrogen) absorption when compared with the case of using copper (Cu) for the metal substrate 52A. This enables the service life of the target 51A to be extended and helps reduce cost per patient of boron capture therapy.

Note that when the embossed structure of the metal substrate 52A of the target 51A according to the present embodiment is formed, this embossed structure may be ordered or irregular. The shapes of the concave recessed portion and the rest island portions may be linear or curved. In FIGS. 4 to 6D, rectangular island portions are arranged on the surface of the metal substrate in the longitudinal and lateral directions with equal spacing. In this way, the recessed portion is created by decreasing the thickness of the metal substrate like a grid in a planar view. In FIG. 6A, the island portions 52b are arranged like what is called "a grid" where the island portions 52b have an identical columnar spacing configuration between the adjacent columns. The present invention, however, is not limited to the present embodiment. The island portions 52b may not have an identical columnar spacing configuration between the adjacent columns. That is, the island portions 52b may be arranged like a "zigzag pattern".

<<Modification Embodiment 1>>

Figure 8A:
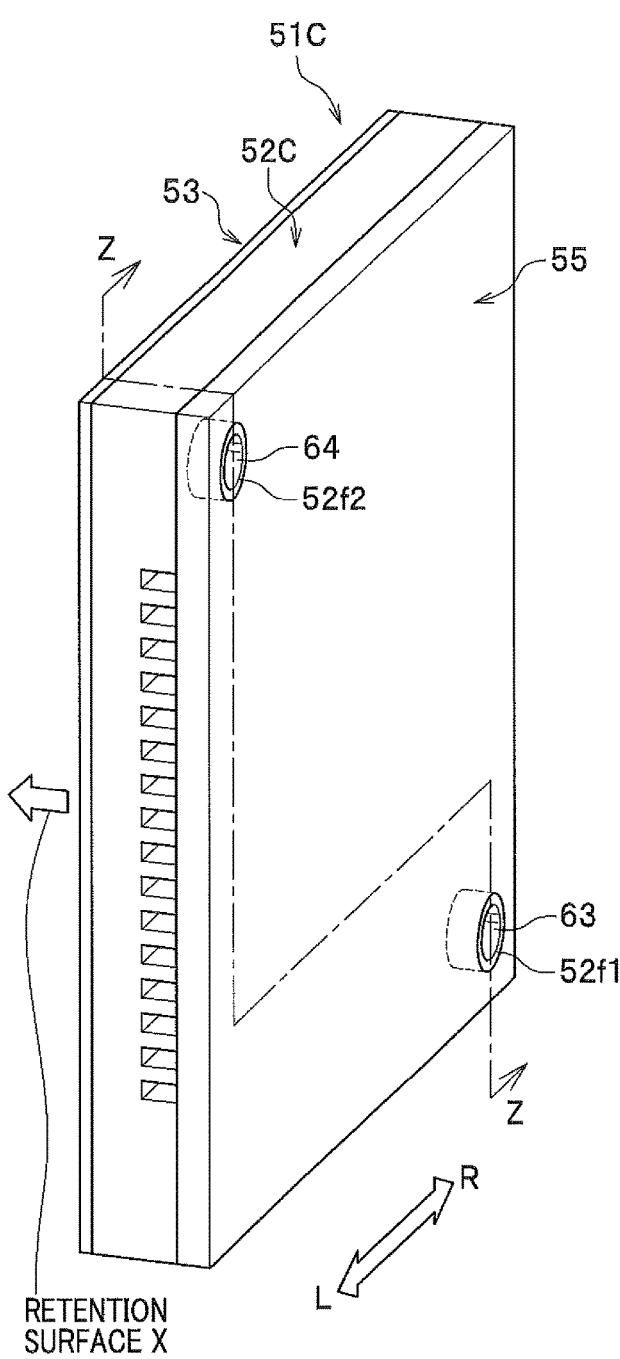
FIGS. 8A-8B illustrate the structure of a target 51C according to a modification embodiment.
Figure 8B:
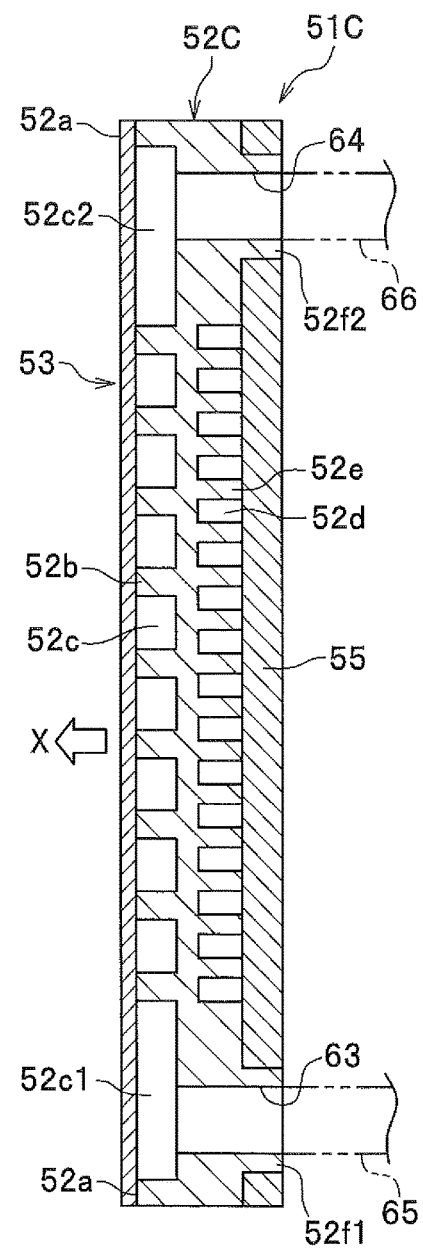
Figure 9:
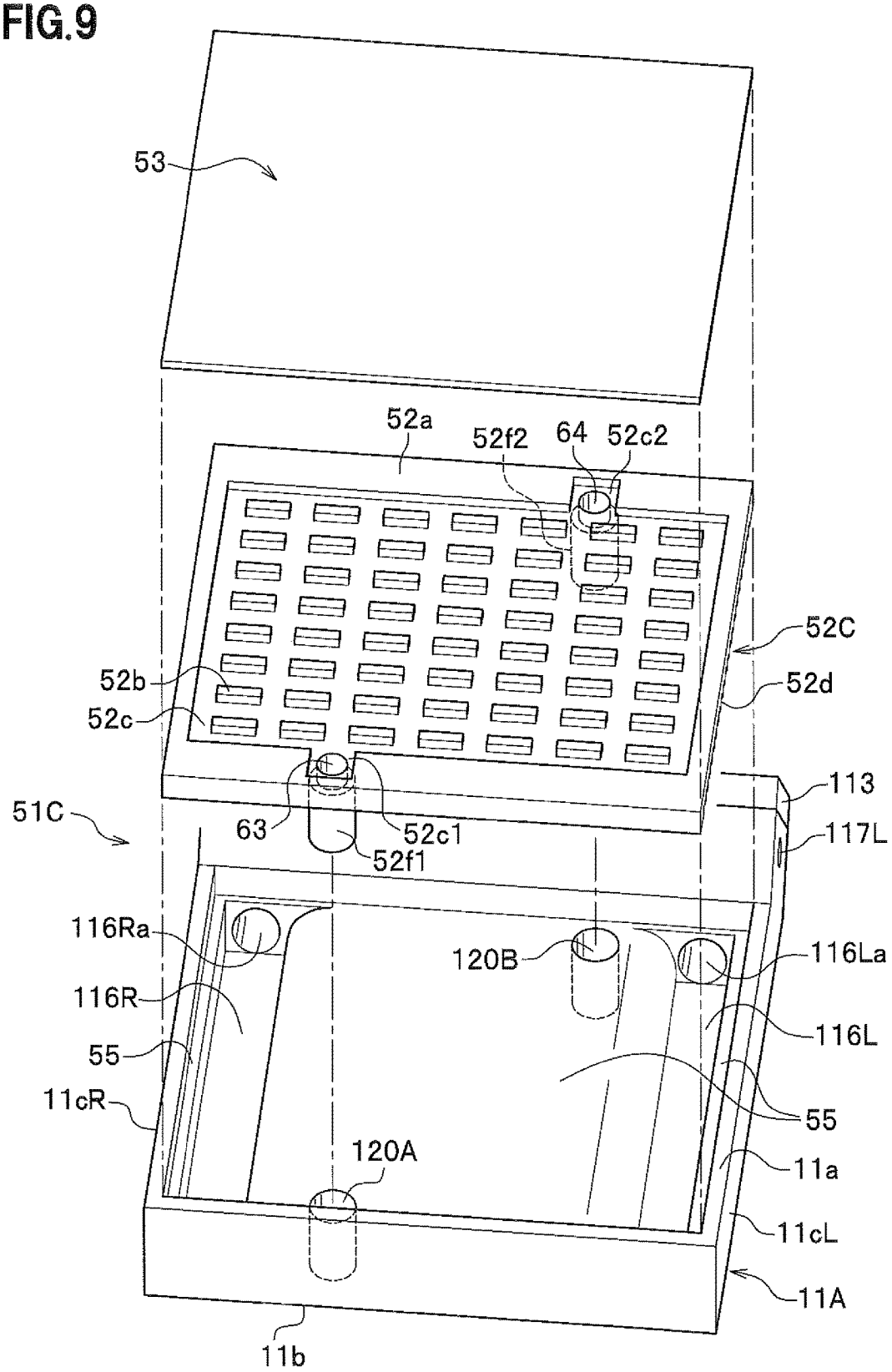
FIG. 9 is an exploded view illustrating the structure of a target panel according to the modification embodiment when viewed from the beam irradiation surface 11a side.
Figure 10:
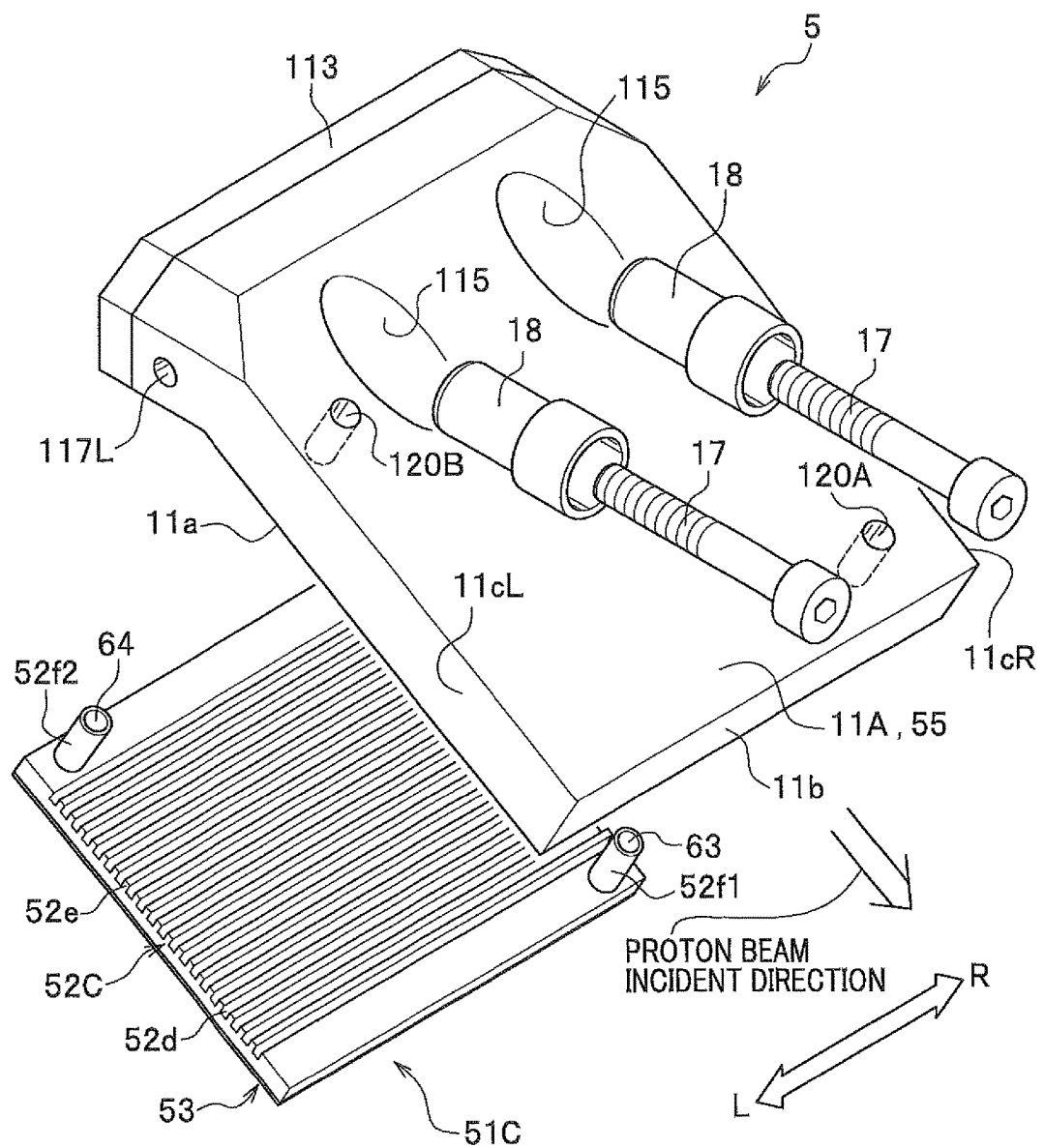
FIG. 10 illustrates how to arrange a molten lithium injection inlet and a filled molten lithium outlet in the target panel according to the modification embodiment.

With reference to FIGS. 8A and 8B, the following illustrates the structure of a target 51C and a method for manufacturing the target 51C. The method differs from that of the target 51A according to the present embodiment. FIGS. 8A and 8B illustrate the structure of the target 51C according to a modification embodiment. FIG. 8A is a schematic perspective view. FIG. 8B is a cross-sectional view taken along the line Z-Z in FIG. 8A. FIG. 9 is an exploded view illustrating the structure of a target panel according to the modification embodiment when viewed from the beam irradiation surface 11a side. FIG. 10 illustrates how to arrange a molten lithium injection inlet and a filled molten lithium outlet in the target panel according to the modification embodiment. The same components as of the target 51A have the same reference signs so as to avoid redundancy.

With regard to the target 51C, FIGS. 8A and 8B provide a schematic view of a metal substrate 52C as a plate. The metal thin film 53 for sealing is attached onto the retention surface X of the metal substrate 52C. The blackboard 55 is attached onto the surface opposite to the retention surface X of the metal substrate 52C. The target 51C differs from the target 51A in the following points. (1) As shown in FIGS. 8A and 8B, two areas near the opposing corners of the retention surface X of the metal substrate 52C include relatively wide rectangular recessed portions 52c1 and 52c2 where no island portions 52b are present. (2) The recessed portion 52c1 is in communication with an injection passage 63; the side opposite to the retention surface X of the metal substrate 52C has, for example, a cylindrical protrusion; a penetrate portion 52f1 has an opening of the injection passage 63 at the end of the protrusion; the recessed portion 52c2 is in communication with an injection passage 64; the side opposite to the retention surface X of the metal substrate 52C has a cylindrical protrusion; and a penetrate portion 52f2 has an opening of the injection passage 64 at the end of the protrusion.

The penetrate portions 52f1 and 52f2 of the metal substrate 52C are positioned closer to the center so as to avoid the manifolds 116L and 116R as shown in FIGS. 9 and 10. The penetrate portions 52f1 and 52f2 are inserted into through holes 120A and 120B, respectively, that penetrate through the flat surface portion of the blackboard 55. The ends of the penetrate portions 52f1 and 52f2 and the surface opposite to the retention surface X of the blackboard 55 (target panel 11A) should be flush. The injection passages 63 and 64 respectively have an opening at the surface opposite to the retention surface X of the target panel 11A.

The same applies to the target panel 11B.

To manufacture the target 51C, the following describes a target material filling step of injecting molten metal lithium. The injection passage 63 is connected to a molten lithium inlet pipe 65 depicted using the imaginary line (two-dot chain line) shown in FIG. 8B. The injection passage 64 is connected to a molten lithium-filled outlet pipe 66 depicted using the imaginary line (two-dot chain line).

After completion of the filling with and solidification of the molten metal lithium, the molten lithium inlet pipe 65 and the molten lithium outlet pipe 66 are cut. Then, the solidified metal lithium is removed from the injection passages 63 and 64. Subsequently, the injection passages 63 and 64 of the penetrate portions 52f1 and 52f2 are capped (not shown), sealed, and welded.

The target 51C is manufactured as follows.

(1) Coolant Passage Formation Step

The original metal substrate 52C is a rectangular low-carbon steel or tantalum plate. In order to form the coolant passages 52d, many grooves are created using, for example, milling on one surface (i.e., the back side (corresponding to the upper surface in FIG. 10)) of the metal substrate to produce cooling fins 52e (see FIG. 10).

(2) Injection Passage Hole-creating Step

Next, holes for the injection passages 63 and 64 are created near the lower right corner and the upper left corner of the metal substrate 52C as shown in FIG. 10.

(3) Embossed Structure Processing Step

The front surface side (corresponding to the upper surface in FIG. 9) of the metal substrate 52C includes: the frame portion 52a; and the plurality of discrete island portions 52b that are surrounded by the frame portion 52a and are regularly arranged in the lateral and longitudinal directions as shown in FIG. 9. The rest recessed portion 52c is created by decreasing the thickness by a predetermined length. For example, the thickness is decreased using milling by 50 μm, which is the same thickness as of the target material metal lithium (Li). At this time, the recessed portion 52c1 is created near the lower left corner by decreasing the thickness by 50 μm in such a manner that the portion invades the frame portion 52a at the lower side as shown in FIG. 9. Further, the recessed portion 52c2 is created near the upper right corner by decreasing the thickness by 50 μm in such a manner that the portion invades the frame portion 52a at the upper side as shown in FIG. 9.

Consequently, as shown in FIG. 9, the bottoms of the recessed portion 52c1 and 52c2 have an opening for the injection passages 63 and 64, respectively, which have been created in the injection passage hole-creating step.

(4) Penetrate Portion-connecting Step

Next, as shown in FIG. 10, the holes for the injection passages 63 and 64 of the metal substrate 52C are welded to the cylindrical penetrate portions 52f1 and 52f2 each having a communication hole for the injection passages 63 and 64.

(5) Bonding Step First, the blackboard 55 (e.g., the blackboard 55 is schematically depicted as a rectangular plate for illustration purpose in FIGS. 8A and 8B) for the target panel 11A (or the target panel 11B) is horizontally placed under an argon gas atmosphere. Next, the back side of the metal substrate 52C is placed on the blackboard 55. Then, the metal thin film 53 for sealing is placed on the retention surface X (see FIG. 8A) of the metal substrate 52C.

At this time, the penetrate portions 52f1 and 52f2 are inserted into the through holes 120A and 120B, respectively, of the blackboard 55 (see FIGS. 9 and 10) of the target panel 11A (or the target panel 11B). The ends of the penetrate portions 52f1 and 52f2 and the surface opposite to the retention surface X of the blackboard 55 of the target panel 11A (or the target panel 11B) should be flush.

After that, an abutting member that is not bonded to the metal thin film 53 during HIP bonding and that has a flat abutting surface facing the metal thin film 53 is placed on the metal thin film 53. Examples of a material for the abutting member include ceramics.

This abutting member has a suitable weight and is to exclude argon gas between the metal thin film 53 and the retention surface X of the metal substrate 52C before the initiation of the HIP bonding. Also, the abutting member makes it possible to keep the flat metal thin film 53 in contact with the retention surface X of the metal substrate 52C during the HIP bonding. This can prevent the metal thin film 53 from being indented into the recessed portions 52c, 52c1, and 52c2.

Thereafter, the HIP bonding is carried out. According to this bonding step, the metal thin film 53 can be bonded to the surfaces of the frame portion 52a and the island portions 52b of the metal substrate 52C while the blackboard 55 is simultaneously bonded to the metal substrate 52C.

At this time, not only the blackboard 55 is bonded to the lower surfaces of the cooling fins 52e of the metal substrate 52C, but also the through holes 120A and 120B of the blackboard 55 are connected to the penetrate portions 52f1 and 52f2, respectively. Further, the circumferential side portions of the metal substrate 52C are also simultaneously bonded to the frame portion of the blackboard 55 at the beam irradiation surface 11a side of the target panel 11A (or the target panel 11B). Consequently, the manifolds 116L and 116R are water tightly attached at the beam irradiation surface 11a side of the target panel 11A (or the target panel 11B).

This bonding step can reduce the number of steps when compared with the bonding step in which the bonding of the metal thin film 53 to the surfaces of the frame portion 52a and the island portions 52b of the metal substrate 52C and the bonding of the blackboard 55 to the metal substrate 52C are separately performed.

(6) Target Material Filling Step

Next, one end of the molten lithium inlet pipe 65 and one end of the molten lithium outlet pipe 66 are welded to the end surfaces of the penetrate portions 52f1 and 52f2 that are exposed at the side opposite to the retention surface X of the blackboard 55 of the target panel 11A (or the target panel 11B). Then, the other end of the molten lithium outlet pipe 66 is connected to a vacuum pump such as an oil diffusion pump. Also, the other end of the molten lithium inlet pipe 65 is connected to a molten metal lithium supplier.

At this time, it is preferable to place the target panel 11A (or the target panel 11B) in a sealed chamber including, for example, a welding device, a cutter, and a heating unit such as an induction heater.

After that, as shown in FIG. 8B, the molten lithium outlet pipe 66 is arranged at the upper side and the molten lithium inlet pipe 65 is arranged at the lower side. Thereafter, the vacuum pump is actuated to vacuum the inside of the molten lithium inlet pipe 65, the spaces occupied by the recessed portions 52c, 52c1, and 52c2 formed between the blackboard 55 and the metal thin film 53, and the inside of the molten lithium outlet pipe 66. In addition, the target panel 11A (or the target panel 11B) is heated using an induction heating process, etc., to a first predetermined temperature of 200° C. or higher, for example, from 400 to 500° C. The target panel 11A (or the target panel 11B) is provided with a plurality of temperature sensors (not shown). Signals from the temperature sensors are used to check whether or not the target panel has been heated to the first predetermined temperature. Then, the recessed portions 52c, 52c1, and 52c2 are filled via the molten lithium inlet pipe 65 with molten metal lithium that is the target material 54 preheated in vacuo to 200° C. or higher.

It is easy to check whether or not the spaces of the recessed portions 52c, 52c1, and 52c2 are sufficiently filled with the molten metal lithium by monitoring the level of the molten metal lithium in the molten lithium outlet pipe 66 by using, for example, X-rays.

After the recessed portions 52c, 52c1, and 52c2 are sufficiently filled with the molten metal lithium, the molten metal lithium supplier side is closed. Then, until the metal substrate 52C, the metal thin film 53, and the molten lithium become wet and have sufficient contacts for a predetermined period, the temperature of the target panel 11A (or the target panel 11B) should be kept for a predetermined period (a retention period) at a second predetermined temperature of 200° C. or higher, for example, from 200 to 300° C. This second predetermined temperature and the retention period are defined in preliminary experiments.

Here, the first predetermined temperature may be high, but is a temperature where the molten metal lithium invades neither the blackboard 55 nor the metal thin film 53 for sealing. This first predetermined temperature should be defined in preliminary experiments. By the way, the first predetermined temperature may be identical to the second predetermined temperature.

(7) Target Material Injection Passage-closing Step

The following describes a step of closing the injection passages 63 and 64 after the filling with the molten metal lithium.

After the retention period has passed, the target is gradually cooled while the spaces of the recessed portions 52c, 52c1, and 52c2 are still filled with the molten metal lithium. Next, the spaces of the recessed portions 52c, 52c1, and 52c2 are filled with the solidified metal lithium. Then, the temperature sensors installed on the target panel 11A (or the target panel 11B) are used to check whether or not the sufficient cooling has been completed. After that, the molten lithium outlet pipe 66 is closed and the vacuum pump is stopped. Thereafter, the sealed chamber including the target panel 11A (or the target panel 11B) is kept in vacuo or under an argon gas atmosphere.

Next, the molten lithium inlet pipe 65 and the molten lithium outlet pipe 66 are cut using the above-mentioned cutter. The metal lithium present in the injection passage 63 of the penetrate portion 52f1 and the injection passage 64 of the penetrate portion 52f2 are cut and removed. Then, caps (not shown), which use the same material as of the metal substrate 52C (not shown), prepared in the sealed chamber are fitted to the injection passages 63 and 64 of the penetrate portions 52f1 and 52f2. After that, the caps are subjected to tight welding such as laser welding and electron beam welding.

The above method is used to complete the target 51C.

Note that in this modification embodiment, the retention period during the target material filling step (6) may be shortened. For this purpose, the "attachment-promoting layer formation step" (3) during the manufacturing of the target 51A of the present embodiment may be included after the embossed structure processing step (3) and before the bonding step (5).

In addition, this modification embodiment includes the target material injection passage-closing step (7) in which the molten lithium inlet pipe 65 and the molten lithium outlet pipe 66 are cut and the injection passages 63 and 64 are capped. The present invention, however, is not limited to this modification embodiment. While the molten lithium inlet pipe 65 and the molten lithium outlet pipe 66 are filled with the molten metal lithium or the solidified metal lithium, the injection passages may be pressed, sealed, and welded.

Further, this modification embodiment includes the penetrate portions 52f1 and 52f2 in the metal substrate 52C. The present invention, however, is not limited to this modification embodiment. The penetrate portions 52f1 and 52f2 may not be provided; HIP bonding may be used to attach the end portions of the through holes 120A and 120B of the blackboard 55 to the hole end portions of the injection passages 63 and 64 of the metal substrate 52C; and the through holes 120A and 120B may thus be part of the injection passages 63 and 64.

In addition to the effects of the above-described embodiment, this modification embodiment can exert an effect of preventing the metal substrate 52A and the metal thin film 53 from being corroded by the placed molten high-temperature target material 54 during the HIP bonding. As a result, the target 51C of this modification embodiment has a longer service life than the target 51A of the present embodiment.

<<Modification Embodiment 2>>

Figure 11B:
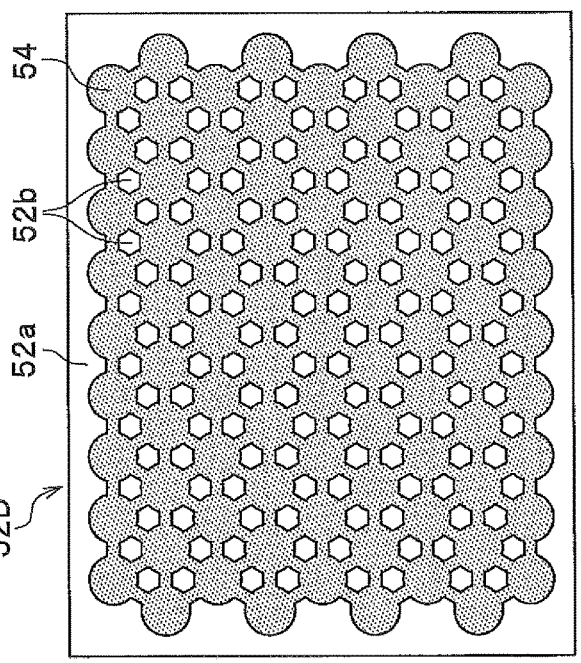
FIGS. 11A-11C illustrate the structure of a target 51D according to another modification embodiment.
Figure 11C:
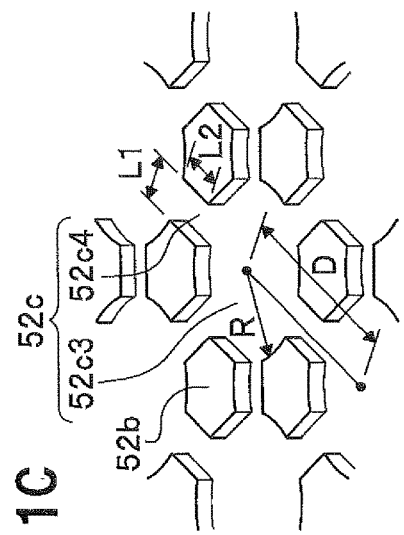
Figure 11A:
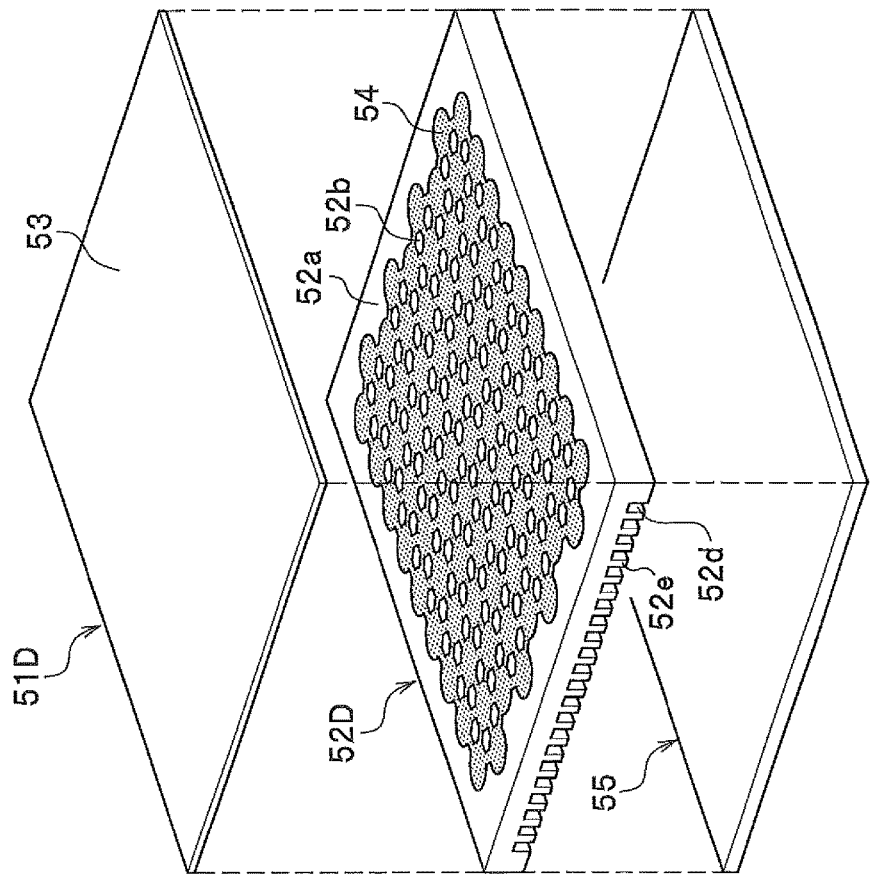

Next, with reference to FIGS. 11A-11C, the following illustrates the structure of a target 51D and a method for manufacturing the target 51D whose embossed structure differs from that of the target 51A of the present embodiment. FIGS. 11A-11C illustrate the structure of the target 51D according to another modification embodiment. FIG. 11A is an exploded view illustrating the target 51D. FIG. 11B is a plan view showing a metal substrate 52D holding the target material 54. FIG. 11C is an enlarged perspective view showing an embossed structure on the metal substrate 52D. The same components as of the target 51A have the same reference signs so as to avoid redundancy.

The target 51D includes: the metal substrate 52D; the target material 54; the metal thin film 53 for sealing; and the blackboard 55. FIG. 11A provides a simplified schematic view of the blackboard 55 as a plate. Like the target 51A, the blackboard 55 is part of the target panel 11A or 11B. Like the blackboard 55 of the target panel 11A (11B) shown in FIG.

4, this blackboard also includes the manifolds 116L and 116R that are concave elongated grooves.

As shown in FIG. 11A, the metal substrate 52D is a substantially rectangular plate and includes the circumferential frame portion 52a at its front surface side (i.e., the upper side in FIG. 11A). The metal substrate 52D also includes: the discrete island portions 52b that are surrounded by the frame portion 52a and are regularly arranged in the lateral and longitudinal directions; and the rest recessed portion 52c where the thickness is decreased. This recessed portion 52c retains the target material 54. The target 51D differs from the target 51A in the shape of an embossed structure formed on the retention surface of the metal substrate 52D.

As shown in FIG. 11B, the embossed structure of the metal substrate 52D includes: a plurality of circular recessed portions that are hexagonally arranged with equal spacing; and communicating recessed portions that are regularly arranged so as to preserve the island portions 52b. Then, the ordered recessed portions hold the target material 54. FIG. 11C is an enlarged perspective view illustrating part of the embossed structure under conditions in which the recessed portions are not filled with the target material 54. In a planar view, the metal substrate 52D includes repeated units of the recessed portion 52c including: a circular recessed portion 52c3 that is circularly created by decreasing the thickness; and rectangular communicating recessed portions 52c4 that are created by decreasing the thickness so as to make communication with the adjacent circular recessed portions 52c3. The island portion 52b, which is a nearly hexagonal cylinder, is positioned at each vertex of a honeycomb structure.

Examples of a preferable material for the metal substrate 52D include low-carbon steel (Fe) and tantalum (Ta). Such an embossed structure can be processed using, for example, milling, electric discharge machining, and/or chemical etching.

The circular recessed portion 52c3 and the communicating recessed portion 52c4 may have the same depth. The surface height of the frame portion 52a is equal to the surface height of each island portion 52b. The step height of the recessed portion 52c is equal to the thickness of the target material metal lithium (Li) and is, for example, 50 μm.

The recessed portion 52c including the circular recessed portions 52c3 and the communicating recessed portions 52c4 is placed beside the rest discrete island portions 52b having a predetermined area. The recessed portion 52c preferably has an area percentage of 70% or more in respect to the area surrounded by the frame portion 52a of the metal substrate 52D. Use of such an area percentage makes it possible to avoid reducing the cross-sectional reaction area of the target material while keeping the surface area of the island portions attached to the metal thin film for sealing.

The circular recessed portion 52c3 may be substantially circular and its size may be the same or different. Also, the circular recessed portions 52c3 may be regularly arranged. For example, the centers of the circular recessed portions 52c3 may be hexagonally arranged with equal spacing. In FIG. 11C, R denotes the radius of the circular recessed portion 52c3 and D denotes the distance between the centers of the adjacent circular recessed portions 52c3. The radius R of the circular recessed portion 52c3 is not particularly limited, but may be from 1 to 5 mm and preferably 2 mm. The distance D between the centers of the adjacent circular recessed portions 52c3 is not particularly limited, but may be from R+1 to R+3 mm and preferably R+1 mm.

Further, the communicating recessed portion 52c4 is preferably a linear groove in communication with each circular recessed portion 52c3. For example, the axes of the communicating recessed portion 52c4 and the line connecting the centers of the adjacent circular recessed portions 52c3 may be the same, which allows the adjacent centers to be connected using the shortest distance. In a planar view, the communicating recessed portion 52c4 may be substantially rectangular. In FIG. 11C, L1 denotes the width of the communicating recessed portion 52c4 and L2 denotes the length of the communicating recessed portion 52c4. The width L1 of the communicating recessed portion 52c4 is not particularly limited, but may be from ⅕ to ½ of the radius of the circular recessed portion 52c3 and preferably ½.

The circular recessed portions 52c3 with a radius of 2 mm may be hexagonally arranged with a 5-mm interval; and the adjacent circular recessed portions 52c3 may then be connected using the communicating recessed portion 52c4 with a length and a width of 1 mm. In this case, the area percentage obtained is about 72% in respect to the area surrounded by the frame portion 52a of the metal substrate 52D.

The thickness from the bottom of the recessed portion 52c to the groove bottom of the coolant passage 52d is a thickness at which all the rest protons passing through the target material 54 irradiated with the proton beams 6 can be blocked.

As shown in FIG. 11A, in the target 51D, the back side of the metal substrate 52D includes: the coolant passages 52d that are created by grooving in the same manner as in the target 51A; and the rest cooling fins 52e.

The recessed portion 52c is filled with metal lithium. Then, the blackboard 55 is placed facing the back side of the metal substrate 52D. Further, the metal thin film 53 for sealing is placed on the upper surface of the metal substrate 52D. After that, HIP bonding is used to attach the metal thin film 53 to the surfaces of the frame portion 52a and the island portions 52b. At the same time, the blackboard 55 is bonded to the back side of the metal substrate 52D.

This target 51D can be manufactured in accordance with the method for manufacturing the above mentioned target 51A.

According to this modification embodiment, the metal lithium that is the target material 54 present in the recessed portion may be heated and melted by proton beam irradiation. Even in this case, the circular recessed portions 52c3 cause the expansion pressure to scatter. The communicating recessed portion 52c4 distributes the melted metal lithium to the adjacent circular recessed portions 52c3, and the melted metal lithium is leveled. When compared with the case of the target 51A according to the above-described embodiment, the expansion of the metal thin film for sealing is more suppressed. Accordingly, the target material 54 and the metal thin film for sealing are kept tightly attached. Hence, this embodiment can reduce the possible occurrence of heat damage of the metal thin film for sealing.

<<Modification Embodiment 3>>

Figure 12A:
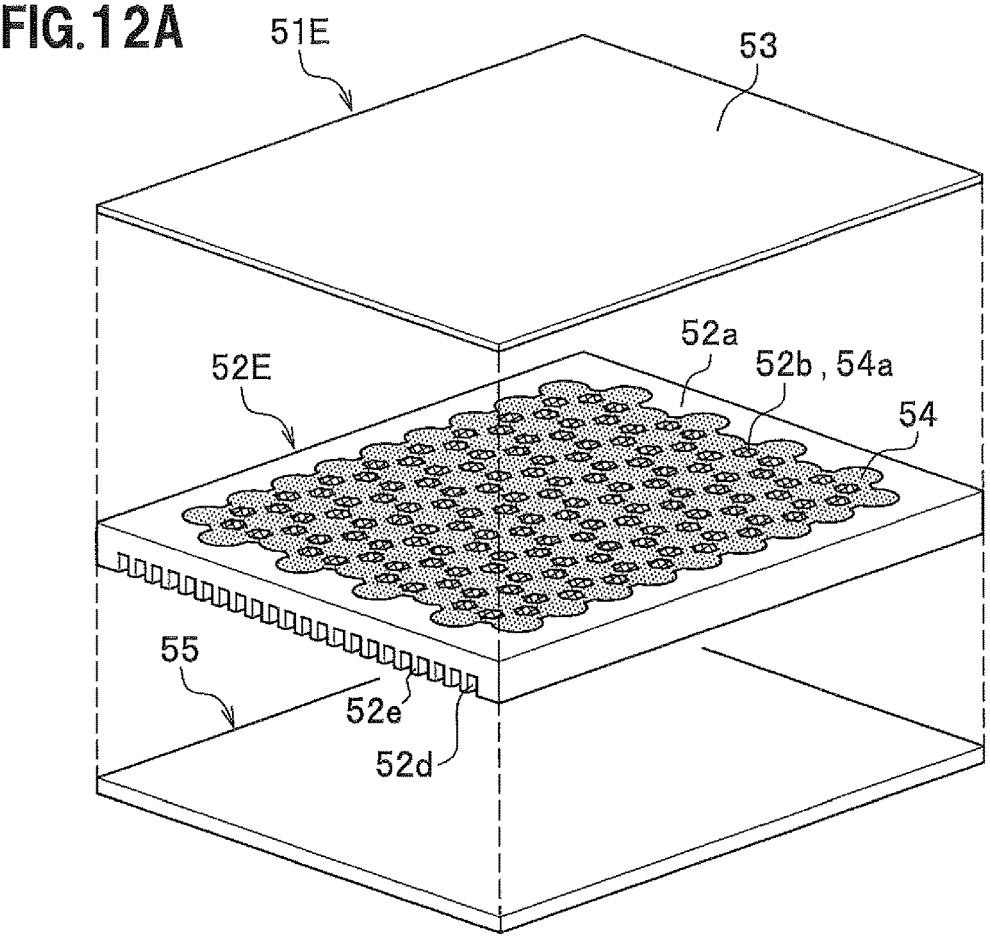
FIGS. 12A-12B illustrate the structure of a target 51E according to still another modification embodiment.
Figure 12B:
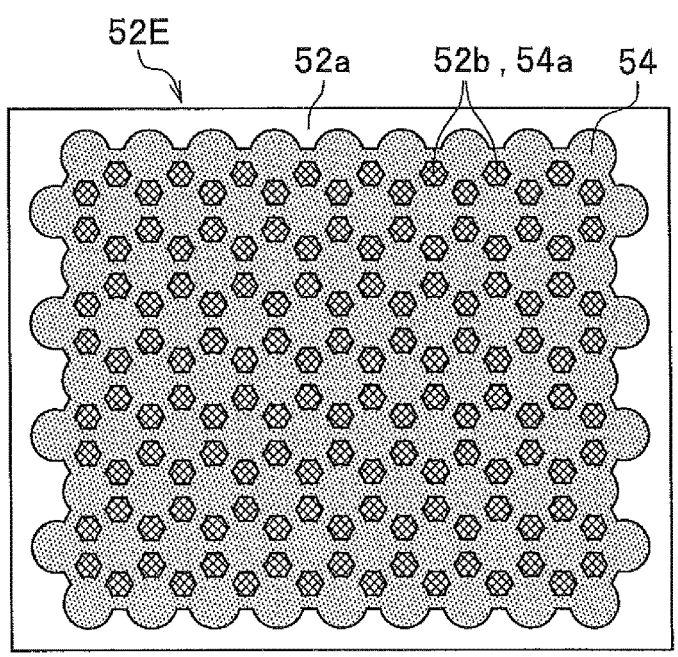

With reference to FIGS. 12A and 12B, the following illustrates the structure of a target 51E and a method for manufacturing the target 51E whose material for the embossed structure differs from that of the target 51D of the above modification embodiment. FIGS. 12A and 12B illustrate the structure of the target 51E according to still another modification embodiment. FIG. 12A is an exploded view illustrating the target 51E. FIG. 12B is a plan view showing a metal substrate 52E holding the target material 54. The same components as of the targets 51A and 51D have the same reference signs so as to avoid redundancy.

The target 51E includes: the metal substrate 52E; the target material 54; the metal thin film 53 for sealing; and the blackboard 55. FIG. 12A provides a simplified schematic view of the blackboard 55 as a plate. Like the target 51A, the blackboard 55 is part of the target panel 11A or 11B. Like the blackboard 55 of the target panel 11A (11B) shown in FIG. 4, this blackboard also includes the manifolds 116L and 116R that are concave elongated grooves.

As shown in FIG. 12A, the front surface side (i.e., the upper side in FIG. 12A) of the substantially rectangular metal substrate 52E includes: the circumferential frame portion 52a; the discrete island portions 52b that are surrounded by the frame portion 52a and are regularly arranged in the lateral and longitudinal directions; and the rest recessed portion 52c where the thickness is decreased.

The target 51E has an embossed structure similar to that of the target 51D. As shown in FIG. 12B, the front surface side of the metal substrate 52E includes: the recessed portion 52c including: the circular recessed portions 52c that are surrounded by the frame portion 52a and that are hexagonally arranged with equal spacing by decreasing the thickness; and the communicating recessed portions 52c4 that are created by decreasing the thickness and that connect the adjacent circular recessed portions 52c3; and the rest substantially hexagonal island portions 52b. Then, the front surface side of the metal substrate 52E holds the target material 54.

The target 51E differs from the target 51D in the material of the island portions 52b of the embossed structure formed on the retention surface of the metal substrate 52E.

In the target 51D, the same material as of the metal substrate 52D is used for the rest island portions 52b while the recessed portion 52c is created by decreasing its thickness. The material may be a non-lithium metal and preferably low-carbon steel (Fe) or tantalum (Ta). By contrast, the island portions 52b of the target 51E are made of a lithium alloy 54a that is the target material 54. Because the material for the island portions 52b s a lithium alloy, the island portions function as a target and are characterized in that they are hard to be melted by heating when compared with the case of using lithium.

Examples of the lithium alloy include alloys that are not melted by heat generated by proton beam irradiation, that is, alloys with a melting point of about 300° C. or higher. Preferable examples used include a copper-lithium alloy, an aluminum-lithium alloy, and a magnesium-lithium alloy.

In the copper-lithium alloy, Cu content is preferably 1 mass % or more and more preferably from 1 to 20 mass %.

In the aluminum-lithium alloy, Al content is preferably 20 mass % or more and more preferably from 20 to 40 mass %.

In the magnesium-lithium alloy, Mg content is preferably 45 mass % or more and more preferably from 45 to 60 mass %.

This modification embodiment exerts the effect of the target 51D. Further, in this modification embodiment, the proton beam irradiation can generate neutrons in the island portions 52b because the island portions 52b are made of alloy containing lithium as the target material 54. Consequently, this modification embodiment can reduce a decrease in a neutron-generating efficiency, by formation of the island portions 52b at the retention surface side of the metal substrate.

As shown in FIG. 12A, in the target 51E, the back side of the metal substrate 52E includes: the coolant passages 52d that are created by grooving in the same manner as in the target 51A; and the rest cooling fins 52e.

The recessed portion 52c is filled with metal lithium. Then, the blackboard 55 is placed facing the back side of the metal substrate 52E. Further, the metal thin film 53 for sealing is placed on the retention surface X of the metal substrate 52E. After that, HIP bonding is used to attach the metal thin film 53 to the surfaces of the frame portion 52a and the island portions 52b. At the same time, the blackboard 55 is bonded to the back side of the metal substrate 52E.

Figure 13A:
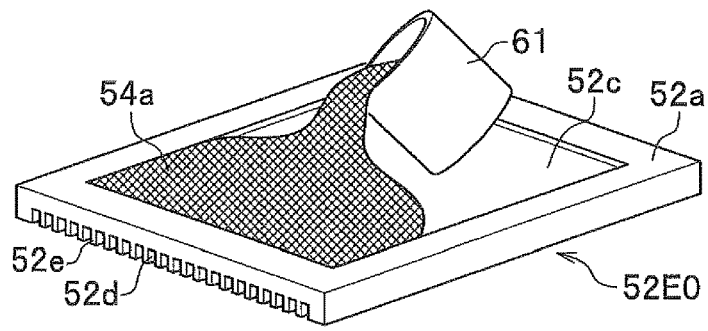
FIGS. 13A-13E illustrates a method for manufacturing the target 51E according to the above modification embodiment.
Figure 13B:
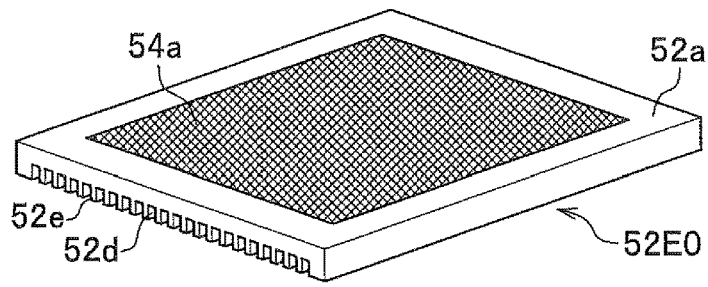
Figure 13C:
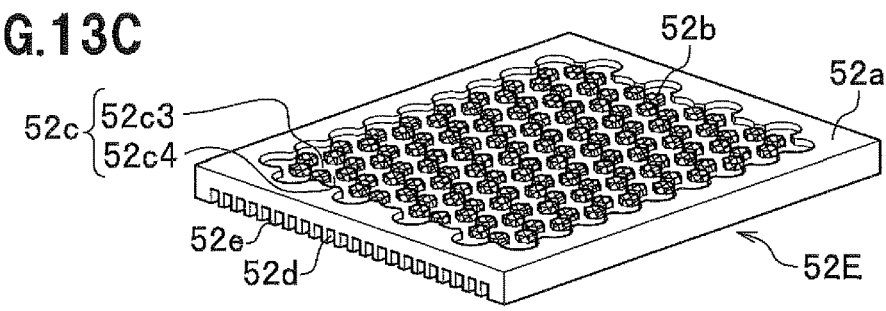
Figure 13D:
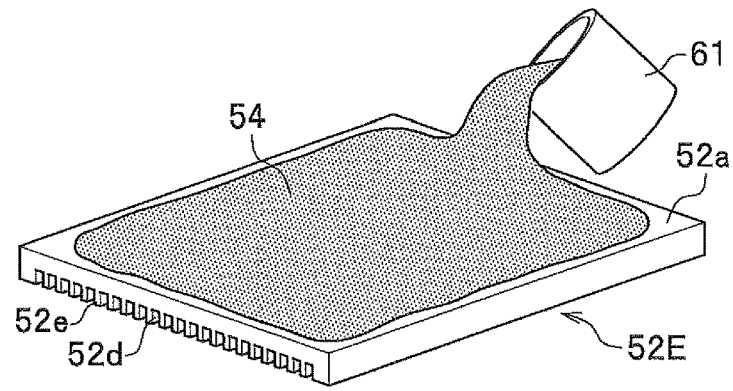
Figure 13E:
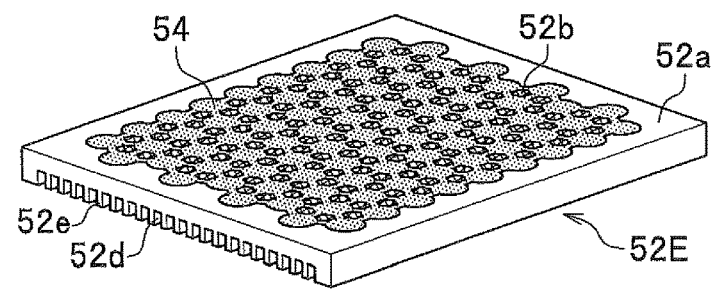

The following illustrates a method for manufacturing the target 51E by referring to FIGS. 13A-13E. FIGS. 13A-13E illustrate how to manufacture the target 51E. FIG. 13A illustrates a method including: a thickness decreasing step of producing a recessed portion 52c by uniformly reducing the thickness of a metal substrate 52E0 of the target 51E at the retention surface side (i.e., the front surface side); a coolant passage creating step of producing grooves for coolant passages 52d at the side (i.e., the back surface side) opposite to the retention surface of the metal substrate 52E0, and thereafter; an attachment-promoting layer formation step of producing an attachment-promoting layer at the bottom of the recessed portion 52c, and thereafter; and a lithium alloy filling step of filling the recessed portion 52c with a melted lithium alloy 54a in vacuo or under an argon gas atmosphere. FIG. 13B illustrates a condition after the lithium alloy filling step, followed by a retention surface smoothing step. FIG. 13C illustrates a condition after an embossed structure processing step. FIG. 13D illustrates another target material filling step of filling the recessed portion 52c with a melted target material 54 in vacuo or under an argon gas atmosphere. FIG. 13E illustrates a condition after the target material filling step, followed by another retention surface smoothing step.

The target 51E is manufactured as follows.

(1) Coolant Passage Formation Step

The original metal substrate 52E is a rectangular low-carbon steel or tantalum plate. In order to form the coolant passages 52d, many grooves are created using, for example, milling on one surface (i.e., the back side (corresponding to the lower surface in FIG. 13A)) of the metal substrate to produce cooling fins 52e (see FIG. 13A).

(2) Thickness-decreasing Step

The thickness of the plate is decreased by a predetermined depth at the front surface side (corresponding to the upper surface in FIG. 13A) while the frame portion 52a is left intact. By doing so, the processed metal substrate 52E0 has a recessed portion 52c with a flat bottom. For example, the thickness is decreased using milling by 50 μm, which is the same thickness as of the target material metal lithium (Li).

(3) Attachment-promoting Layer Formation Step

After the thickness-decreasing step, a very thin layer (or attachment-promoting layer) made of copper, aluminum, magnesium, or zinc is deposited using a film formation process such as vapor deposition and sputtering on the bottom of the recessed portion 52c. The thickness of the layer is, for example, 0.05 μm. This process makes better the attachment (or wearability) between the metal substrate 52E0 and the lithium alloy 54a. At this time, before the film formation process such as vapor deposition and sputtering, the surface of the frame portion 52a is masked so as not to form a copper thin layer. After the film formation process such as vapor deposition and sputtering, the mask is ripped off.

(4) Lithium Alloy Filling Step

Next, a molten lithium alloy 54a contained in a crucible 61 is poured into the recessed portion 52c of the metal substrate 52E0 in vacuo or under an argon gas atmosphere (see FIGS. 13A and 13B). Because argon gas contains oxygen and moisture content ($H_2O$) as impurities, the molten lithium alloy 54a may be oxidized. Hence, it is preferable to fill the recessed portion 52c with the lithium alloy in vacuo. The placed lithium alloy 54a is then solidified as it is in vacuo or under an argon gas atmosphere.

(5) Retention Surface Smoothing Step

The solidified lithium alloy 54a is attached onto the surface of the frame portion 52a, and the level of the lithium alloy 54a is also higher than the surface of the frame portion 52a. So, the lithium alloy is ground using, for example, milling. The resulting powder of the lithium alloy 54a is then removed by, for example, blowing with argon gas (see FIG. 13B). Because argon gas contains oxygen and moisture content ($H_2O$) as impurities, the molten metal lithium may be oxidized. Hence, it is preferable to grind the surface in vacuo.

(6) Embossed Structure Processing Step

Next, in a planar view, circular structures with a predetermined depth are created by decreasing the thickness of the lithium alloy 54a with which the recessed portion 52c has been filled. For example, the thickness of the lithium alloy 54a is decreased to produce the structures with a diameter of 4 mm and a depth that reaches the metal substrate at the bottom of the recessed portion 52c. The structures are created using, for example, milling so as to hexagonally arrange the structures in the longitudinal and lateral directions. By doing so, the circular recessed portions 52c3 are formed.

Further, communicating recessed portions 52c4 with a predetermined shape are created by decreasing the thickness of the lithium alloy 54a so as to connect the adjacent circular recessed portions 52c3. For example, the thickness of the lithium alloy 54a is decreased to produce the communicating recessed portions 52c4 with a width of 1 mm and a depth that reaches the metal substrate at the bottom of the recessed portion 52c.

Then, the communicating recessed portions 52c4 are used to connect all the circular recessed portions 52c3. By doing so, the metal substrate 52E is produced that has an embossed structure including: a plurality of island portions 52b made of the lithium alloy 54a; and the recessed portion 52c (see FIG. 13C).

(7) Attachment-Promoting Layer Formation Step

After the embossed structure processing step, a very thin layer (or attachment-promoting layer) made of copper, aluminum, magnesium, or zinc is deposited using a film formation process such as vapor deposition and sputtering on the bottom of the recessed portion 52c. The thickness of the layer is, for example, 0.05 µm. This process makes better the attachment (or wearability) between the metal substrate 52E and lithium that is the target material 54. At this time, before the film formation process such as vapor deposition and sputtering, the upper surfaces (in FIG. 13C) of the frame portion 52a and the island portions 52b are masked so as not to form a copper thin layer. After the film formation process such as vapor deposition and sputtering, the mask is ripped off.

(8) Target Material Filling Step

Next, molten metal lithium, which is the target material 54, contained in a crucible 61 is poured into the recessed portion 52c in vacuo or under an argon gas atmosphere (see FIG. 13D). Because argon gas contains oxygen and moisture content ($H_2O$) as impurities, the molten metal lithium may be oxidized. Hence, it is preferable to fill the recessed portion 52c with the metal lithium in vacuo. The placed metal lithium, which is the target material 54, is solidified as it is in vacuo or under an argon gas atmosphere.

(9) Retention Surface Smoothing Step

The solidified metal lithium is attached onto the surfaces of the frame portion 52a and the island portions 52b, and the level of the metal lithium is also higher than the surfaces of the frame portion 52a and the island portions 52b. So, the metal lithium is ground using, for example, milling. The resulting metal lithium powder is then removed by, for example, blowing with argon gas. As a result, the surfaces of the frame portion 52a and the island portions 52b are exposed in a clean state. This makes only the recessed portion 52c filled with the metal lithium (see FIG. 13E). Because argon gas contains oxygen and moisture content ($H_2O$) as impurities, the molten metal lithium may be oxidized. Hence, it is preferable to grind the surface in vacuo.

(10) Bonding Step

Subsequently, in the same manner as in the method for manufacturing the target 51A, the blackboard 55, the metal substrate 52E, and the metal thin film 53 of the target panel 11A (or the target panel 11B) are subjected to HIP bonding under an argon gas atmosphere.

The above method is used to complete the target 51C.

<<Modification Embodiment 4>>

Figure 14:
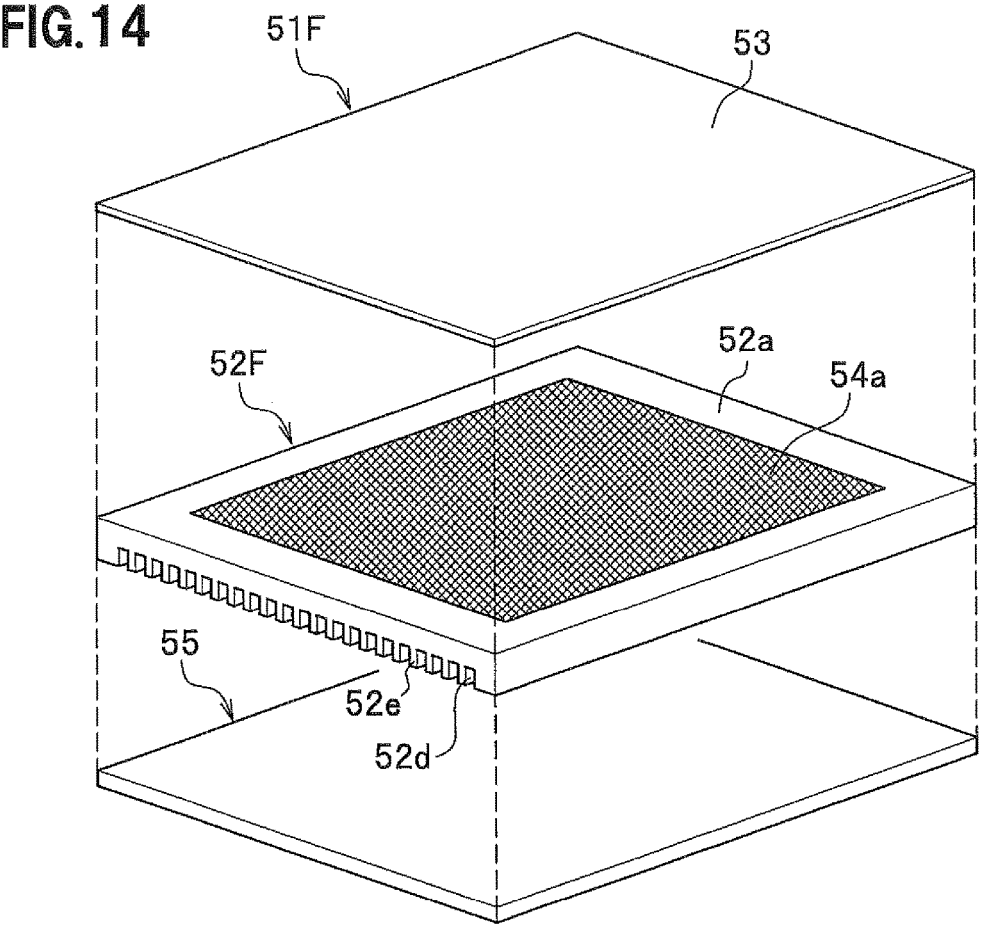
FIG. 14 is an exploded view illustrating a target 51F according to still another modification embodiment.

With reference to FIG. 14, the following illustrates the structure of a target 51F and a method for manufacturing the target 51F whose structure of the recessed portion and material for the target material 54 differ from those of the target 51A of the present embodiment. FIG. 14 is an exploded view illustrating the target 51F according to still another modification embodiment. The same components as of the target 51A have the same reference signs so as to avoid redundancy.

The target 51F includes: a metal substrate 52F; the target material 54; the metal thin film 53 for sealing; and the blackboard 55. FIG. 14 provides a simplified schematic view of the blackboard 55 as a plate. Like the target 51A, the blackboard 55 is part of the target panel 11A or 11B. Like the blackboard 55 of the target panel 11A (11B) shown in FIG. 4, this blackboard also includes the manifolds 116L and 116R that are concave elongated grooves.

As shown in FIG. 14, the front surface side (i.e., the upper side in FIG. 14) of the substantially rectangular metal substrate 52F includes: the circumferential frame portion 52a; and the recessed portion 52c that is surrounded by the frame portion 52a and that is uniformly concave. The recessed portion 52c of the metal substrate 52F has a flat bottom. Like the target 51B of the comparative embodiment, no embossed structure is formed.

The target 51F differs from the target 51B in the material for the target material 54 with which the recessed portion 52c is filled.

Here, the recessed portion 52c of the target 51B is filled with pure metal lithium, as the target material 54, containing essentially 100 mass % of lithium.

By contrast, the recessed portion 52c of the target 51F is filled with the lithium alloy 54a as the target material 54. The lithium alloy 54a is a target material 54 characterized in that the lithium alloy 54a is hard to be melted by heat when compared with metal lithium.

Examples of the lithium alloy 54a include lithium alloys that are not melted by heat generated by proton beam irradiation. Namely, a lithium alloy has a melting point of about 300° C. or higher and contains an additional metal at a decreased small % so as not to shorten the travel distance of the proton beams through the lithium alloy. Preferable examples used include a copper-lithium alloy, an aluminum-lithium alloy, and a magnesium-lithium alloy.

In the copper-lithium alloy, Cu content is preferably from 1 to 20 mass %. In the aluminum-lithium alloy, Al content is preferably from 20 to 40 mass %. In the magnesium-lithium alloy, Mg content is preferably from 45 to 60 mass %.

Examples of a preferable material for the metal substrate 52F include low-carbon steel (Fe) and tantalum (Ta). The recessed portion 52c with a flat bottom can be processed using, for example, milling, electric discharge machining, and/or chemical etching.

The step height difference between the frame portion 52a and the recessed portion 52c is the same as the thickness of the target material and is, for example, 50 µm.

The thickness from the bottom of the recessed portion 52c to the groove bottom of the coolant passage 52d is a thickness at which all the rest protons passing through the target material 54 irradiated with the proton beams 6 can be blocked.

As shown in FIG. 14, in the target 51F, the back side of the metal substrate 52F includes: the coolant passages 52d that are created by grooving in the same manner as in the target 51A; and the rest cooling fins 52e.

The recessed portion 52c is filled with the lithium alloy 54a. Then, the blackboard 55 is placed facing the back side of the metal substrate 52D. Further, the metal thin film 53 for sealing is placed on the upper surface of the metal substrate 52F. After that, HIP bonding is used to attach the metal thin film 53 to the surface of the frame portion 52a. At the same time, the blackboard 55 is bonded to the back side of the metal substrate 52F.

This target 51F is manufactured as follows: the metal substrate 52Be is filled with the lithium alloy 54a in accordance with the method for manufacturing the above target 51E; the retention surface smoothing step is carried out; and the HIP bonding step is then performed.

Alternatively, the metal thin film 53 for sealing is pressed on the lithium alloy 54a that has been subjected to rolling at a predetermined thickness; they are placed on a metal substrate without the recessed portion 52c and further pressed; and the metal thin film 53 for sealing is welded onto the substrate circumference of the metal substrate.

This modification embodiment has the advantage compared with the case of using relatively low-melting-point metal lithium as the target material 54. That is, when low-melting-point metal lithium is used as the target material 54, the target material 54 may be heated and melted by proton beam irradiation. The liquefied target material 54 is unevenly distributed at one portion of the metal substrate.

By contrast, this modification embodiment using a lithium alloy as the target material 54 can prevent the target material 54 from being melted. Thus, it is possible to prevent the liquefied target material 54 from being unevenly distributed at one portion of the metal substrate, thereby preventing target performance from being deteriorated.

REFERENCE OF SIGNS

1 Proton beam-generating unit
1a Ion source
1b Accelerator
2 Irradiation unit
3 Treatment unit
4 Beam conduit
5 Target section
Proton beams
7 Beam-condensing lens
9 Neutron beams
10 Collimator
10a Tip flange part
11A, 11B Target panel
11a Beam irradiation surface
11b End surface
11cL, 11cR Panel side surface
12L, 12R Side plate
17 Mounting bolt
18 Insulation piece
21 Moderate
22 Reflector
23 Neutron absorber
24 Collimator
51A, 51B, 51C, 51D, 51E, 51F Target
52A, 52B, 52C, 52D, 52E, 52F Metal substrate
52a Frame portion
52b Island portion
52c Recessed portion
52c3 Circular recessed portion
52c4 Communicating recessed portion
52d Coolant passage
52e Cooling fin
53 Metal thin film for sealing
54 Target material
54a Target material (Lithium alloy)
55 Blackboard
Crucible
100 Neutron-generating device
112 Beam stopper
113, 124 Insulator
115 Mounting hole
116L, 116R Manifold
116La, 116Ra, 117L, 117R, 121L, 121R, 123L, 123R Coolant passage hole
122L, 122R Coolant channel

The invention claimed is:

1. A target for a neutron-generating device that generates neutrons by using a $^7$Li(p,n)$^7$Be reaction while lithium as a target material is irradiated with proton beams accelerated by an accelerator, the target comprising:
   a metal substrate that retains the target material; and
   a metal thin film for sealing that seals the target material onto the metal substrate at a retention surface side holding the target material,
   the metal substrate comprising: on the retention surface side,
      a frame portion; and
      an embossed structure comprising:
         a plurality of discrete island portions surrounded by the frame portion and regularly arranged in lateral and longitudinal directions, the island portions having the same height as the frame portion; and
         a recessed portion that is created by decreasing a thickness of a region other than the frame portion and the plurality of island portions by a thickness of the target material,
   wherein the metal thin film for sealing is bonded to surfaces of the frame portion and the plurality of island portions and configured to keep a thickness of the target material even when the target material is melted while being irradiated with the proton beams,
   wherein the metal thin film for sealing is configured to seal the target material onto the recessed portion of the metal substrate, and the target material is tightly attached to the metal thin film for sealing.

2. The target for a neutron-generating device according to claim 1, wherein the recessed portion of the embossed structure comprises: a plurality of circular recessed portions that are hexagonally arranged inside the surrounding frame portion and are circular in a planar view; and communicating recessed portions in communication with the adjacent circular recessed portions.

3. The target for a neutron-generating device according to claim 1, wherein a bottom of the recessed portion has an attachment-promoting layer that causes the target material to better attach to the metal substrate.

4. The target for a neutron-generating device according to claim 3, wherein the attachment-promoting layer is a thin film layer made of copper, aluminum, magnesium, or zinc.

5. The target for a neutron-generating device according to claim 1, wherein the metal substrate further comprises a plurality of elongated coolant passages through which a coolant flows at a surface side opposite to the retention surface side.

6. The target for a neutron-generating device according to claim 1, wherein the metal substrate is made of iron or tantalum and the metal thin film for sealing is made of a stainless steel sheet, titanium sheet, titanium alloy sheet, beryllium sheet, or beryllium alloy sheet.

7. The target for a neutron-generating device according to claim 1, wherein the island portions of the embossed structure are made of a lithium alloy comprising any of 1 to 20 mass % of Cu, 20 to 40 mass % of Al, and 45 to 60 mass % of Mg, and the remainder consisting of Li and unavoidable impurities.

8. A method for manufacturing a target for a neutron-generating device that generates neutrons by using a $^7$Li(p, n)$^7$Be reaction while lithium as a target material is irradiated with proton beams accelerated by an accelerator, the method comprising:
   an embossed structure processing step of producing an embossed structure comprising: on a retention surface side of a metal substrate holding the target material, a frame portion for sealing the target material; a plurality of discrete island portions that are surrounded by the frame portion and regularly arranged in lateral and longitudinal directions and that have the same height as of the frame portion; and a recessed portion that is created by decreasing a thickness of a region other than the island portions by a thickness of the target material;
   an attachment-promoting layer formation step of producing an attachment-promoting layer at a bottom of the recessed portion, the layer causing the target material to better attach to the metal substrate;
   a target material filling step of filling the recessed portion at the retention surface side with the target material so that a level of the target material is higher than surfaces of the frame portion and the island portions, and thereafter;
   a retention surface smoothing step of grinding and leveling the target material thus solidified so that the surfaces of the frame portion and the island portions are exposed; and
   a bonding step of bonding a metal thin film for sealing the target material to the recessed portion of the metal substrate onto the surfaces of the frame portion and the island portions at the retention surface side by using hot isostatic pressing (HIP) bonding so that the target material is tightly attached to the metal thin film for sealing and a thickness of the target material is kept even when the target material is melted while being irradiated with the proton beams.

9. A method for manufacturing a target for a neutron-generating device that generates neutrons by using a $^7$Li(p, n)$^7$Be reaction while lithium as a target material is irradiated with proton beams accelerated by an accelerator, the method comprising:
   an embossed structure processing step of producing an embossed structure comprising: on a retention surface side of a metal substrate holding the target material, a frame portion for sealing the target material; a plurality of discrete island portions that are surrounded by the frame portion and regularly arranged in lateral and longitudinal directions and that have the same height as of the frame portion; and a recessed portion that is created by decreasing a thickness of a region other than the island portions by a thickness of the target material;
   a bonding step of bonding a metal thin film for sealing the target material to the recessed portion of the metal substrate onto surfaces of the frame portion and the island portions at the retention surface side by using hot isostatic pressing (HIP) bonding; and
   a target material filling step comprising:
      heating the metal substrate after the bonding step to a first predetermined temperature of 200° C. or higher;
      injecting the target material thus preheated and melted into the metal thin film-covered recessed portion of the metal substrate to be sufficiently filled with the target material;
      keeping the target material at a second predetermined temperature equal to or less than the first predetermined temperature until contact surfaces between the target material and the metal thin film and between the target material and the metal substrate become sufficiently wet and have no gap so that a thickness of the target material is kept even when the target material is melted while being irradiated with the proton beams.

10. The method for manufacturing a target for a neutron-generating device according to claim 9, the method further comprising an attachment-promoting layer formation step of producing an attachment-promoting layer at a bottom of the recessed portion, the layer causing the target material to better attach to the metal substrate, wherein the attachment-promoting layer formation step is placed after the embossed structure processing step and before the bonding step.

* * * * *